US006933117B2

(12) United States Patent
Wolf et al.

(10) Patent No.: US 6,933,117 B2
(45) Date of Patent: Aug. 23, 2005

(54) REAGENTS AND METHODS FOR AUTOMATED HYBRIDIZATION

(75) Inventors: Catherine Wolf, Eckbolsheim (FR); Hiroaki Nitta, Oro Valley, AZ (US); Thomas Grogan, Tucson, AZ (US); Jacques Cavadenti, Strasbourg (FR); Lidija Pestic-Dragovich, Tucson, AZ (US); Anthony Hartman, Tucson, AZ (US); Angela Sattler, Tucson, AZ (US); Jennifer Wong, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

(21) Appl. No.: 10/136,714

(22) Filed: Apr. 30, 2002

(65) Prior Publication Data

US 2003/0044823 A1 Mar. 6, 2003

Related U.S. Application Data

(60) Provisional application No. 60/287,324, filed on Apr. 30, 2001, and provisional application No. 60/287,325, filed on Apr. 30, 2001.

(51) Int. Cl.[7] .......................... C12Q 1/68; C12P 19/34; C07H 21/02; C07H 21/04
(52) U.S. Cl. .................... 435/6; 435/91.1; 536/23.1; 536/24.3
(58) Field of Search .................... 435/6, 91.1, 810, 435/501, 7.8, 77, 78; 536/23.1, 24.3; 422/64, 67, 100, 82.12, 141, 145, 104; 436/43, 45, 501, 518, 800, 808

(56) References Cited

U.S. PATENT DOCUMENTS

| | | | |
|---|---|---|---|
| 5,002,867 A | 3/1991 | Macevicz | 435/6 |
| 5,143,854 A | 9/1992 | Pirrung et al. | 436/518 |
| 5,202,231 A | 4/1993 | Drmanac et al. | 435/6 |
| 5,225,326 A * | 7/1993 | Bresser et al. | 435/6 |
| 5,487,975 A * | 1/1996 | Miller et al. | 435/7.5 |
| 5,665,546 A * | 9/1997 | Cubbage et al. | 435/6 |
| 5,688,290 A * | 11/1997 | Bjork et al. | 8/401 |
| 5,700,637 A | 12/1997 | Southern | 435/6 |
| 5,861,242 A | 1/1999 | Chee et al. | 435/5 |
| 6,004,755 A | 12/1999 | Wang | 435/6 |
| 6,033,860 A | 3/2000 | Lockhart et al. | 435/6 |
| 6,045,996 A | 4/2000 | Cronin et al. | 435/6 |
| 6,054,270 A | 4/2000 | Southern | 435/6 |
| 6,296,809 B1 | 10/2001 | Richards et al. | 422/64 |
| 6,579,688 B2 * | 6/2003 | Steaffens et al. | 435/7.92 |
| 6,656,685 B2 * | 12/2003 | Utermohlen et al. | 435/6 |
| 2002/0048591 A1 * | 4/2002 | Cole et al. | 424/401 |

FOREIGN PATENT DOCUMENTS

| | | |
|---|---|---|
| WO | WO 92/10092 | 6/1992 |
| WO | WO 93/17126 | 9/1993 |
| WO | WO 99/06599 | 2/1999 |
| WO | WO 99/40430 | 8/1999 |
| WO | WO 00/14507 * | 3/2000 |

OTHER PUBLICATIONS

Sambrook et al., Molecular Cloning, A Laboratory Manual, Cold Spring Harbor Laboratory 1989.*

Stratagene catalog (1988, p. 39).*

Schena et al. "Parallel human genome analysis: Microarray–based expression monitoring of 1000 genes" Proc. Natl. Acad. Sci vol. 93, pp. 10614–10619, Oct. 1996.*

Tokuda, Y. "Mechanism of DNA degradation in formaldehyde–fixed tissues and its use for molecular pathology" Kobe Daigaku Igakubu Kiyo (1990), 51(2), abstract.*

"CRC Handbook of Biochemistry and Molecular Biology, Physical and Chemical Data", CRC Press, Boca Raton, Florida, 3rd Edition, (vol. 1, p. 371, 1984).*

Ausubel et al. ("Short Protocols in Molecular Biology", Third Edition, John Wiley & Sons, p. A1–13, 1997).*

Weiss, L. M. et al., "Effects of Different Fixatives on Detection of Nucleic Acids from Paraffin–Embedded Tissues by In Situ Hybridization Using Oligonucleotide Probes", J. Histochem. Cytochem., vol. 39, pp. 1237–1242 (1991).*

Andrechek et al., "Amplification of the *neu/erbB–2* oncogene in a mouse model of mammary tumorigenesis," *PNAS* 97(7):3444–3449 (2000).

Beaucage et al., "Deoxynucleoside Phosphoramidites—A New Class of Key Intermediates for Deoxypolynucleotide Synthesis," *Tetrahedron Letters* 22(20):1859–1862 (1981).

Heller et al., "Discovery and analysis of inflammatory disease–related genes using cDNA microarrays," *Proc. Natl. Acad. Sci. USA* 94:2150–2155 (1997).

Matteucci et al., "Synthesis of Deoxyoligonucleotides on a Polymer Support," *J. Am. Chem. Soc.* 103:3185–3191 (1981).

Schena et al., "Parallel human genome analysis: Microarray–based expression monitoring of 1000 genes," *Proc. Natl. Acad. Sci. USA* 93:10614–10619 (1996).

(Continued)

*Primary Examiner*—Jeffrey Fredman
*Assistant Examiner*—Teresa Strzelecka
(74) *Attorney, Agent, or Firm*—McDonnell Boehnen; Hulbert & Berghoff LLP

(57) ABSTRACT

The invention provides novel reagents, reagent kits, and methods for automated hybridization. More particularly, the invention provides reagents, reagent kits, and methods for automated in situ hybridization and automated hybridization on a microarray. The use of automated instruments for in situ hybridization and microarray hybridization dramatically reduces the amount of labor and time involved and also facilitates standardization of protocols and consistency between results.

33 Claims, 2 Drawing Sheets

OTHER PUBLICATIONS

Houggard, et al. "Non–Radioactive In Situ Hybridization for Mrna with Emphasis on the Use of Oligodeoxynucleotide Probes", *Histochem Cell Biol,* pp. 335–344 (1997).

Cheung et al., "Making and Reading Microarrays", *Nature Genetics,* pp. 15–19 (1999).

Rimsza, et al., "Rapid Automated Combined in Situ Hybridization and Immunohistochemically for Sensitive Detection of Cytomegalovirus in Paraffin–Embedded Tissue Biopsies", *American Journal of Clinical Pathology,* pp. 544–548 (1996).

Rundle et al., "In Situ Hybridization Analysis of Immunoglobulin Heavy Chain Variable Gene Expression with Family Specific Oligonucleotide Probes", *Journal of Immunological Methods,* pp. 31–52 (1998).

Karr et al., "In Situ Hybridization for cytokine mRNA with Digoxigenin–labeled Riboprobes. Sensitivity of detected and double label applications", *Journal of Immunological Methods,* pp. 93–106 (1995).

* cited by examiner

*Comparison of Discovery™ and Manual Hybridization Techniques
(Signal-to-Background)*

REAGENTS AND METHODS FOR AUTOMATED HYBRIDIZATION

CROSS-REFERENCE TO RELATED APPLICATIONS

This application claims priority from U.S. Provisional Patent Application No. 60/287,325, filed Apr. 30, 2001, entitled "Automated Immunohistochemical and In Situ Hybridization Assay Formulations." This application incorporates U.S. Provisional Patent Application No. 60/287,325 by reference in its entirety.

This application also claims priority from U.S. Provisional Patent Application No. 60/287,324, filed Apr. 30, 2001, entitled "Reagents and Methods for Automated Hybridization." This application incorporates U.S. Provisional Patent Application No. 60/287,324 by reference in its entirety.

BACKGROUND OF THE INVENTION

1. Field of the Invention

The invention relates to the fields of medicine, genetics, biochemistry and molecular biology. In particular, the invention relates to reagents, reagent kits, and methods for automated hybridization. More particularly, the invention relates to reagents, reagent kits, and methods for automated in situ hybridization and automated hybridization on microarrays.

2. Description of the Related Art

Nucleic acid hybridization reactions can be used to detect and characterize specific nucleotide sequences in both DNA and RNA molecules. For example, Southern blotting involves the extraction of DNA from cells or tissues and may be used to determine the genetic structure of a particular chromosome. Similarly, Northern blotting involves the extraction of RNA from cells or tissue and may be used to determine whether and how much of a particular mRNA is present in a certain tissue. Additional assay formats for detecting nucleic acids by hybridization include the following: nuclear run-on assays; slot blot assays; magnetic particle separation; reverse Northern blot assays; dot blot assays; RNase protection assays; ligase chain reaction (LCR); polymerase chain reaction (PCR); reverse transcriptase-PCR (RT-PCR); differential display RT-PCR (DDRT-PCR); in situ hybridization; and, more recently, microfabricated arrays (also referred to as "microarrays" or "gene chips"). In each of these formats, detection methods that may be employed include, among others, radioactive labels; enzyme labels; chemiluminescent labels; and fluorescent labels.

In situ hybridization is a powerful technique for, among other uses, identifying the subcellular location of nucleic acids. Since nucleic acids, no less than other macromolecules, occupy precise positions in cells and tissues, a great deal of potential information is lost when nucleic acids are extracted by homogenization. For this reason, techniques have been developed in which nucleic acid probes are used to locate specific nucleic acid sequences in situ, a procedure called in situ hybridization (ISH). ISH may be performed to analyze either DNA or RNA in cells.

In ISH analysis of DNA, labeled nucleic acid probes are hybridized to chromosomes that have been exposed briefly to very high pH or high temperature to disrupt their DNA base pairs. The chromosomal regions that bind the probe during the hybridization step are then visualized. Originally, this technique was developed using highly radioactive DNA probes, which were detected by autoradiography. The spatial resolution of the technique, however, can be greatly improved by labeling the DNA probes chemically instead of radioactively. For this purpose the probes are synthesized with special nucleotides that contain a modified side chain, and the hybridized probes are detected with an antibody (or other ligand) that specifically recognizes this side chain.

RNA in situ hybridization methods can reveal the distribution of specific RNA molecules in cells and tissues. In this case the tissues are not exposed to high pH or temperature, so the chromosomal DNA remains double-stranded and cannot bind the probe. Instead the tissue is fixed so that RNA is retained in an exposed form capable of hybridizing with a complementary DNA or RNA probe. In this way the patterns of differential gene expression can be observed in tissues.

In situ hybridization of mRNA is useful to study disease, identify potential therapeutic targets, and evaluate candidate drugs. For example, the diagnosis of breast, ovarian, and other carcinomas may be facilitated by techniques that determine the presence and expression of the c-erb2/HER-2/neu protooncogene. The c-erb2/HER-2/neu protooncogene is a member of the epidermal growth factor receptor (EGFR) family of receptor tyrosine kinases. Amplification and overexpression of the c-erb2/HER-2/neu protooncogene is found in about 30% of breast carcinomas and about 20% of ovarian carcinomas. Andrecheck et al. (2000) Proc. Natl. Acad. Sci. USA 97:3444.

Either DNA or RNA probes may be used for in situ hybridization. Typically, an RNA probe ("riboprobe") is made by in vitro transcription of a cloned cDNA that encodes the gene of interest. Thus, one must have a vector containing the cDNA flanked by promoters, such as T7 and T3 promoters, in order to make a riboprobe. On the other hand, a DNA oligonucleotide probe ("oligoprobe") may be prepared, for example, using an automated DNA synthesizer. Thus, one of skill in the art needs to know only the sequence of the gene of interest to make an oligoprobe. An additional advantage of oligoprobes for in situ hybridization is that they are more stable than riboprobes. A further advantage of oligoprobes is that, because of their short length, access and hybridization to a target may be facilitated. In addition to oligoprobes and riboprobes, DNA/RNA hybrid probes (i.e., those containing both deoxyribonucleotides and ribonucleotides) and probes containing modified nucleic acids may be used for in situ hybridization.

Instruments for the automation of in situ hybridization have recently been developed. For example, see U.S. Pat. No. 6,296,809, which is hereby incorporated by reference in its entirety. Such instruments are programmable and capable of performing in situ hybridization on multiple samples such that each sample is subject to its own staining and treatment protocol, even when each sample requires its own temperature parameters. Additionally, samples requiring de-waxing (e.g., tumor sections) can be automatically processed at the same time as other samples that do not require this preliminary step (e.g., smears). Thus, automated instruments dramatically reduce the labor and time involved in in situ hybridization, and also facilitate standardization of protocols and consistency between results.

Microarrays are arrays of many nucleic acids having different sequences, printed in specific locations in a small area on a substrate such as a glass slide. Hybridization on a microarray ("microarray hybridization") is a powerful technique for, among other uses, simultaneously determining the expression levels of many different genes in a cell or tissue sample. For example, Schena et al. (1996) used microarrays to quantitatively monitor differential expression of heat shock and phorbol ester-regulated genes in human T cells. Schena et al. (1996) Proc. Natl. Acad. Sci. U.S.A. 93:10614. Similarly, Heller et al. (1997) demonstrated the use of gene chips to profile expression of selected human genes involved in inflammation, as well as genes expressed in peripheral human blood cells. Heller et al. (1997) Proc. Natl. Acad. Sci. U.S.A. 94:2150.

In addition, arrays of oligonucleotide probes immobilized on solid supports have been used to determine specific nucleic acid sequences in a target nucleic acid. For example, U.S. Pat. Nos. 5,202,231 and 5,002,867, as well as International Publication No. WO 93/17126, relate to the use of large numbers of oligonucleotide probes to provide the complete nucleic acid sequence of a target nucleic acid molecule.

Additional methods of using microarrays are disclosed in the following U.S. Patents, each of which is hereby incorporated by reference in its entirety. Southern (U.S. Pat. Nos. 5,700,637 and 6,054,270) discloses an apparatus and method for analyzing a polynucleotide sequence in order to perform gene polymorphism studies, genomic fingerprinting analysis, linkage analysis, mRNA characterization, gene expression studies, and sequence determinations. The polynucleotide sequence to be analyzed is labeled and applied to an array of oligonucleotides that are capable of taking part in hybridization reactions with the polynucleotide sequence. Chee (U.S. Pat. No. 5,861,242) discloses an array of oligonucleotide probes immobilized on a solid support for the analysis of a target sequence from a human immunodeficiency virus. Wang (U.S. Pat. No. 6,004,755) discloses methods for quantitative gene expression analysis in which an end-labeled target nucleic acid is contacted with an array of probe molecules stably associated with the surface of a solid support under hybridization conditions sufficient to produce a hybridization pattern. The resultant hybridization pattern is used to obtain quantitative information about the genetic profile of the end-labeled target nucleic acid sample, as well as the physiological source from which it is derived. Lockhart (U.S. Pat. No. 6,033,860) discloses probe collections immobilized on solid supports that are highly differentially expressed among developmental stages and organs. The probes can be used to prioritize potential drug targets, to monitor disease progression and remission, and to assess drug metabolism. Lockhart (U.S. Pat. No. 6,040,138) discloses methods of monitoring the expression levels of a multiplicity of genes. The methods involve hybridizing a nucleic acid sample to a high-density array of oligonucleotide probes where the high-density array contains oligonucleotide probes complementary to subsequences of target nucleic acids in the nucleic acid sample. Cronin (U.S. Pat. No. 6,045,996) discloses methods of performing nucleic acid hybridization assays on high-density substrate-bound oligonucleotide arrays, wherein the hybridization mixture includes an isostabilizing agent, a denaturing agent, or a renaturation accelerant.

There is a need in the art for reagents and methods for automated hybridization. In situ hybridization applications for use with existing automated instruments have not yet been developed. Moreover, manual manipulation of microarrays is tedious and time-consuming, and thus there is also a need for methods for automated microarray hybridization. The automation of such processes would have wide application in the medical, genetic, biochemical, and molecular biological arts. In addition, there is a need for reagents that can be used in automated in situ hybridization and automated microarray hybridization. Furthermore, there is a need for reagent kits for use in automated in situ hybridization and automated microarray hybridization.

BRIEF SUMMARY OF THE INVENTION

The invention relates to reagents, reagent kits, and methods for automated hybridization. More particularly, the invention relates to reagents, reagent kits, and methods for automated in situ hybridization and automated hybridization on microarrays.

One composition of the invention comprises sodium chloride; sodium phosphate dibasic; sodium phosphate monobasic; EDTA; first primary prehybridization detergent; second primary prehybridization detergent; and formalin.

A further composition of the invention comprises sodium citrate; citric acid; cell conditioning preservative; and nonionic detergent.

A further composition of the invention comprises sodium chloride; phosphate buffer; EDTA; and one or more nonionic detergents.

A further composition of the invention comprises 4x–8x SSPE and 8–12% spreading enhancer detergent.

A further composition of the invention comprises phosphate buffer of any total salt concentration; proteinaceous material; and nonionic detergent.

One reagent kit of the invention for use in in situ hybridization comprises: (a) an aqueous composition, comprising 0.15–1.5 M sodium chloride; 8–80 mM sodium phosphate dibasic; 2–20 mM sodium phosphate monobasic; 1–10 mM EDTA; 0.0125–0.125% first primary prehybridization detergent; 0.00375–0.0375% second primary prehybridization detergent; and 10–40% formalin; (b) an aqueous composition, comprising 0.1–1 N HCl; and (c) an aqueous composition, comprising 1x–5xSSPE; 10–50% dextran sulfate sodium salt, average molecular weight 10,000; 50–80% formamide; and 0.01–1% in situ hybridization detergent.

A reagent kit of the invention for use in automated microarray hybridization comprises: (a) an aqueous composition, comprising 4x–8xSSPE and 8–12% spreading enhancer detergent; (b) an aqueous composition, comprising phosphate buffer of 10–200 mM total salt concentration; 0.5–6% goat gamma globulins; 5–15% hydrolyzed casein; and 0.005–1% nonionic detergent; (c) an aqueous composition, comprising 2–6xSSPE; 17.5–22.5% dextran sulfate sodium salt, average molecule weight 10,000; and 10–50% formamide; and (d) an aqueous composition, comprising 0.1–5% microarray cleaning detergent.

One method for automated in situ hybridization of the invention comprises: (a) exposing a cell or tissue sample to a prehybridization solution; (b) exposing the sample to a cell conditioning reagent; (c) exposing the sample to a nucleic acid probe in a hybridization solution; (d) exposing the sample to a wash solution; (e) exposing the sample to a post-hybridization fixing solution; and (f) analyzing the sample for hybridization between the probe and a target nucleic acid; wherein steps (a)–(e) are performed using an automated instrument.

A method for automated microarray hybridization of the invention comprises: (a) exposing a microarray to a spreading enhancer solution; (b) exposing the microarray to a blocking solution; (c) exposing the microarray to a target nucleic acid in a hybridization solution; (d) exposing the microarray to a wash solution; (e) exposing the microarray to a microarray cleaning solution; and (f) analyzing the microarray for hybridization between a nucleic acid probe and the nucleic acid target; wherein steps (a), (b), (d), and (e) are performed using an automated instrument.

DETAILED DESCRIPTION OF THE INVENTION

Figure 1:
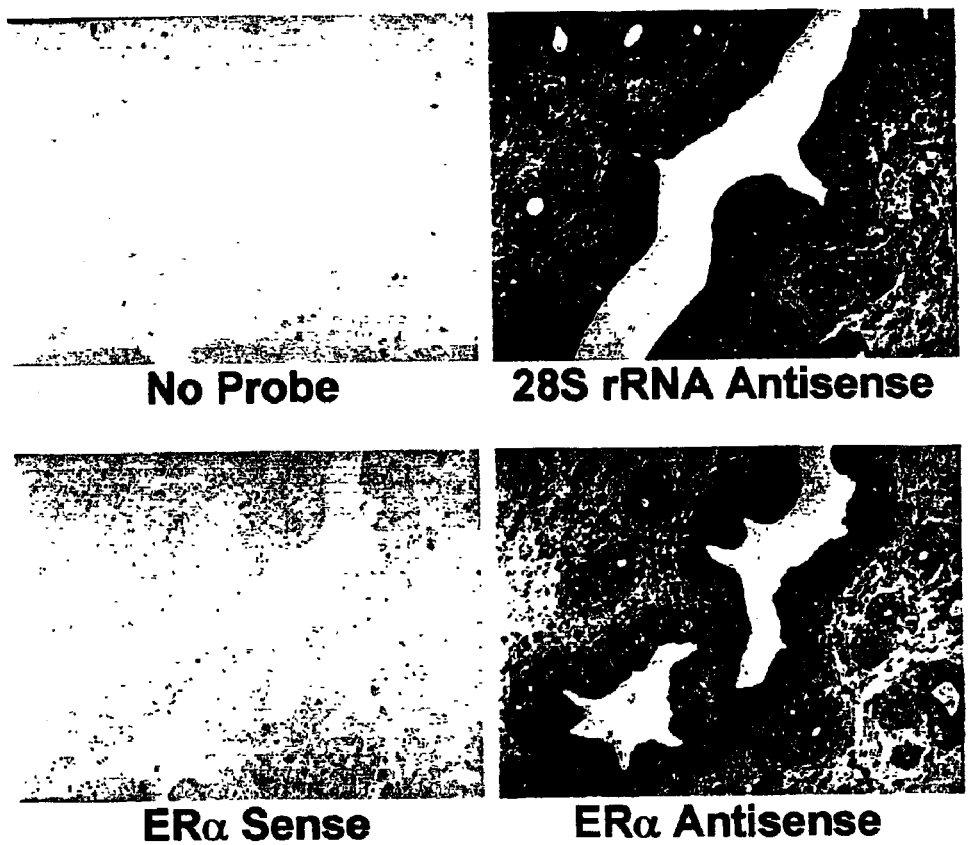
FIG. 1 shows the results of automated in situ hybridization of mouse oviduct tissue using oligoprobes for 28S rRNA (control) and ERα (test).

The methods, reagents, and kits of the invention are for automated hybridization. The term "automated hybridization" refers to methods of hybridization that involve the use of automated instruments. "Automated hybridization" includes, but is not limited to, automated in situ hybridization and automated microarray hybridization.

"Prehybridization solution" refers to a solution that is useful for application to tissue samples prior to the hybridization step in methods for automated in situ hybridization. "Prehybridization solution" includes "primary prehybridization solution" and "secondary prehybridization solution."

"Primary prehybridization solution" refers to an aqueous solution useful for treating tissue samples prior to hybridization, including for fixing samples after deparaffinization. In one embodiment, primary prehybridization solution is an aqueous solution comprising sodium chloride; sodium phosphate dibasic; sodium phosphate monobasic; EDTA; "first primary prehybridization detergent"; "second primary prehybridization detergent"; and formalin. In a preferred embodiment, primary prehybridization solution comprises 0.15–1.5 M sodium chloride; 8–80 mM sodium phosphate dibasic; 2–20 mM sodium phosphate monobasic; 1–10 mM EDTA; 0.0125–0.125% first primary prehybridization detergent; 0.00375–0.0375% second primary prehybridization detergent; and 10–40% formalin. In a most preferred embodiment, primary prehybridization solution comprises 0.3 M sodium chloride; 16 mM sodium phosphate dibasic; 4 mM sodium phosphate monobasic; 2 mM EDTA; 0.025% first primary prehybridization detergent; 0.0075% second primary prehybridization detergent; and 30% formalin and is referred to as "RIBOPREP™."

"First primary prehybridization detergent" is a constituent of primary prehybridization solution. In a preferred embodiment, first primary prehybridization detergent is a nonionic detergent that comprises octylphenol ethylene oxide condensate. In a most preferred embodiment, first primary prehybridization detergent is a product obtained from Sigma-Aldrich, Inc., St. Louis, Mo., in 2000, having Product No. 21123, and sold under the trademark TRITON® X-100. TRITON® X-100 is a registered trademark of Union Carbide Corp.

"Second primary prehybridization detergent" is another constituent of primary prehybridization solution. In a preferred embodiment, second primary prehybridization detergent is a nonionic detergent that comprises polyoxyethylene (23) lauryl ether, having a molecular formula of $C_{12}H_{25}(OCH_2CH_2)_nOH$, n~23. In a most preferred embodiment, second primary prehybridization detergent is a product obtained from Sigma-Aldrich, Inc., St. Louis, Mo., in 2000, having Product No. 858366, and sold under the trademark BRIJ® 35. BRIJ® 35 is a registered trademark of ICI Americas, Inc.

"Secondary prehybridization solution" refers to a hydrochloric acid solution suitable as a secondary pretreatment reagent in in situ hybridization protocols. In a preferred embodiment, secondary prehybridization solution comprises 0.1–1 N HCl. In a most preferred embodiment, secondary prehybridization solution comprises 0.3 N HCl and is referred to as "RIBOCLEAR™."

"Cell conditioning reagent" refers to an aqueous solution useful for conditioning cell samples prior to hybridization in methods of in situ hybridization. For example, cell conditioning reagents include those disclosed in U.S. patent application Ser. No. 09/800,689, filed Mar. 7, 2001, which is hereby incorporated by reference in its entirety.

"Cell conditioning solution" is an example of a cell conditioning reagent. In one embodiment, cell conditioning solution comprises sodium citrate; citric acid; "cell conditioning preservative"; and nonionic detergent. In a preferred embodiment, the nonionic detergent is "cell conditioning detergent." In a more preferred embodiment, cell conditioning solution comprises 0.4–8.2 mM sodium citrate; 1.8–10 mM citric acid; 0.1–1% cell conditioning preservative; and 0.05–5% cell conditioning detergent. In a most preferred embodiment, cell conditioning solution comprises 8.2 mM sodium citrate; 1.8 mM citric acid; 0.05% cell conditioning preservative; and 0.1% cell conditioning detergent and is referred to as "RIBOCC™."

"Cell conditioning preservative" is a constituent of cell conditioning solution. In a preferred embodiment, cell conditioning preservative comprises 5-chloro-2-methyl-4-isolthiazolin-3-one; 2-methyl-4-isolthiazolin-3-one; modified glycol; and alkyl carboxylate. In a more preferred embodiment, cell conditioning preservative comprises 2.30% 5-chloro-2-methyl-4-isolthiazolin-3-one; 0.70% 2-methyl-4-isolthiazolin-3-one; 94–95% modified glycol; and 2–3% alkyl carboxylate. In a most preferred embodiment, cell conditioning preservative is a product obtained from Sigma-Aldrich, Inc., St. Louis, Mo., in 2000, having Catalog No. 48125, and sold under the trademark PROCLIN® 300. PROCLIN® 300 is a registered trademark of Rohm and Haas Company.

"Cell conditioning detergent" is another constituent of cell conditioning solution. In a preferred embodiment, cell conditioning detergent comprises polyoxyethylene(20) sorbitan monolaurate. In a most preferred embodiment, cell conditioning detergent is a product obtained from Sigma-Aldrich, Inc., St. Louis, Mo., in 2000, having Product No. 274348, and sold under the trademark TWEEN® 20. TWEEN® 20 is a registered trademark of ICI Americas, Inc.

"Hybridization solution" refers to an aqueous solution useful for hybridizing a nucleic acid probe to a target nucleic acid. "Hybridization solution" includes "in situ hybridization solution" and "microarray hybridization solution."

"In situ hybridization solution" refers to an aqueous solution useful for hybridizing a probe to a target nucleic acid in in situ hybridization methods. In one embodiment, in situ hybridization solution comprises SSPE; dextran sulfate sodium salt, average molecular weight 10,000; formamide; and nonionic detergent. In a further embodiment, the nonionic detergent in is "in situ hybridization detergent." In a preferred embodiment, in situ hybridization solution comprises 1×–5×SSPE; 10–50% dextran sulfate sodium salt, average molecular weight 10,000; 50–80% formamide; and 0.01–1% in situ hybridization detergent. In a most preferred embodiment, in situ hybridization solution comprises 2×SSPE; 20% dextran sulfate sodium salt, average molecular weight 10,000; 80% formamide; and 0.05% in situ hybridization detergent and is referred to as "RIBOHYBE™." RIBOHYBE™ is disclosed in U.S. patent application Ser. No. 09/772,123, filed Jan. 29, 2001, which is hereby incorporated by reference in its entirety.

"In situ hybridization detergent" is a constituent of in situ hybridization solution. In a preferred embodiment, in situ hybridization detergent is a nonionic detergent that comprises polyoxyethylene(23) lauryl ether, having a molecular formula of $C_{12}H_{25}(OCH_2CH_2)_n OH$, n~23. In a most preferred embodiment, in situ hybridization detergent is a product obtained from Sigma-Aldrich, Inc., St. Louis, Mo., in 2000, having Product No. 858366, and sold under the trademark BRIJ® 35.

SSPE, which is another constituent of in situ hybridization solution, is a common buffer used in many biochemical methods. SSPE comprises 3 M NaCl; 40 mM sodium phosphate monobasic; 160 mM sodium phosphate dibasic; and 20 mM EDTA.

"Microarray hybridization solution" refers to an aqueous solution useful for hybridizing a probe to a target nucleic acid on a microarray. In one embodiment, microarray hybridization solution comprises SSPE; dextran sulfate sodium salt, average molecular weight 10,000; and formamide. In a most preferred embodiment, microarray hybridization solution comprises 6×SSPE; 20% dextran sulfate sodium salt, average molecular weight 10,000; and 10% formamide and is referred to as "CHIPHYBE™." CHIPHYBE™ is disclosed in U.S. patent application Ser. No. 09/772,123, filed Jan. 29, 2001.

"Wash solution" refers to an aqueous solution useful for washing samples after the hybridization step in in situ hybridization methods and microarray hybridization methods. Wash solution is useful for washing samples either when an RNA probe (riboprobe) or a DNA probe (oligoprobe) is used. In one embodiment, wash solution comprises sodium chloride; phosphate buffer; EDTA; and one or more nonionic detergents. In a preferred embodiment, wash solution comprises two nonionic detergents: "first wash detergent" and "second wash detergent." In a more preferred embodiment, wash solution comprises 0.1–0.5 M sodium chloride; 5–30 mM sodium phosphate dibasic; 1–10 mM sodium phosphate monobasic; 0.5–5 mM EDTA; 0.01–0.1% first wash detergent; and 0.0025–0.025% second wash detergent. In a most preferred embodiment, wash solution comprises 0.3 M sodium chloride; 16 mM sodium phosphate dibasic; 4 mM sodium phosphate monobasic; 2 mM EDTA; 0.025% first wash detergent; and 0.0075% second wash detergent and is referred to as "RIBOWASH™."

"First wash detergent" is a constituent of wash solution. In a preferred embodiment, first wash detergent is a nonionic detergent that comprises octylphenol ethylene oxide condensate. In a most preferred embodiment, first wash detergent is a product obtained from Sigma-Aldrich, Inc., St. Louis, Mo., in 2000, having Product No. 21123, and sold under the trademark TRITON® X-100.

"Second wash detergent" is another constituent of wash solution. In a preferred embodiment, second wash detergent is a nonionic detergent that comprises polyoxyethylene(23) lauryl ether, having a molecular formula of $C_{12}H_{25}(OCH_2CH_2)_n OH$, n~23. In a most preferred embodiment, second wash detergent is a product obtained from Sigma-Aldrich, Inc., St. Louis, Mo., in 2000, having Product No. 858366, and sold under the trademark BRIJ® 35.

It is convenient to package and distribute wash solution in a concentrated form. In one embodiment of the concentrated form, wash solution comprises 0.5–2.5 M sodium chloride; 25–150 mM sodium phosphate dibasic; 5–50 mM sodium phosphate monobasic; 2.5–25 mM EDTA; 0.05–0.5% first wash detergent; and 0.0125–0.125% second wash detergent. In a most preferred embodiment of the concentrated form, wash solution comprises 1.5 M sodium chloride; 80 mM sodium phosphate dibasic; 20 mM sodium phosphate monobasic; 10 mM EDTA; 0.125% first wash detergent; and 0.0375% second wash detergent.

"Post-hybridization fixing solution" is useful for fixing samples after hybridization in methods for in situ hybridization. In one embodiment, post-hybridization fixing solution is identical to an embodiment of primary prehybridization solution. In a preferred embodiment, post-hybridization fixing solution is identical to a preferred embodiment of primary prehybridization solution. In a most preferred embodiment, post-hybridization fixing solution is identical to a most preferred embodiment of primary prehybridization solution and is referred to as "RIBOFIX™." "RIBOFIX™" is identical to "RIBOPREP™."

"Spreading enhancer solution" (SES) is useful for reducing non-specific hybridization and ensuring initial slide surface coverage in methods for automated microarray hybridization. In one embodiment, SES comprises a buffer (e.g., SSPE) and a nonionic detergent. In a preferred embodiment, SES comprises 4×–8×SSPE and 8–12% "spreading enhancer detergent." In a most preferred embodiment, SES comprises 6×SSPE and 10% spreading enhancer detergent and is referred to as "CHIPPREP™ 1."

"Spreading enhancer detergent" is a constituent of spreading enhancer solution. In a preferred embodiment, spreading enhancer detergent comprises polyoxyethylene(20) sorbitan monolaurate. In a most preferred embodiment, spreading enhancer detergent is a product obtained from Sigma-Aldrich, Inc., St. Louis, Mo., in 2000, having Product No. 274348, and sold under the trademark TWEEN® 20.

"Blocking solution" is useful for preventing nonspecific binding of a labeled target to a nucleic acid on a microarray. In one embodiment, blocking solution comprises phosphate buffer of any total salt concentration; proteinaceous material (e.g., gamma globulins, casein, or any other protein suitable for blocking nonspecific binding); and nonionic detergent. In a preferred embodiment, blocking solution comprises phosphate buffer of 10–200 mM total salt concentration; 0.5–6% goat gamma globulins; 5–15% hydrolyzed casein; and 0.005–1% nonionic detergent. In a most preferred embodiment, blocking solution comprises 75 mM potassium phosphate; 25 mM sodium phosphate; 55 mM NaCl; 3% goat gamma globulins; 13.4% hydrolyzed casein; and 0.05% "blocking detergent" and is referred to as "CHIPPREP™ 2."

"Blocking detergent" is a constituent of blocking solution. In a preferred embodiment, blocking detergent is a nonionic detergent that comprises polyoxyethylene(23) lauryl ether, having a molecular formula of $C_{12}H_{25}(OCH_2CH_2)_n OH$, n~23. In a most preferred embodiment, blocking detergent is a product obtained from Sigma-Aldrich, Inc., St. Louis, Mo., in 2000, having Product No. 858366, and sold under the trademark BRIJ® 35.

"Microarray cleaning solution" is useful for removing LIQUID COVERSLP™ (see, e.g., U.S. Pat. Nos. 5,225,325 and 5,418,138, each of which is hereby incorporated by reference in its entirety) from a microarray following the hybridization and washing steps of microarray hybridization methods, thereby reducing the background signal observed upon analysis of the microarray. Microarray cleaning solution comprises "microarray cleaning detergent" diluted in water, preferably deionized water. In a preferred embodiment, microarray cleaning solution comprises 0.1–5% microarray cleaning detergent. In a most preferred embodiment, microarray cleaning solution comprises 1% microarray cleaning detergent and is referred to as "CHIPCLEAN™."

"Microarray cleaning detergent" is a constituent of microarray cleaning solution and refers to any detergent that effectively removes LIQUID COVERSLIP™ from a microarray. In a preferred embodiment, microarray cleaning detergent comprises biodegradable anionic and nonionic surfactants and no phosphate. In a most preferred embodiment, microarray cleaning detergent is a product manufactured by Procter & Gamble, Inc., Cincinnati, Ohio, 45202, obtained in 2001, having UPC number 3700091342, 3700030840, or 3700035986, disclosed in U.S. Pat. Nos. 5,990,065 and 6,069,122 (both of which are hereby incorporated by reference), and sold under the trademark DAWN®. DAWN® is a registered trademark of Procter & Gamble, Inc.

The "RIBOMAP™" kit is designed for automated in situ hybridization, although it may also be used for manual methods of in situ hybridization. The RIBOMAP™ kit may be used in in situ hybridization protocols with formalin-fixed or paraformaldehyde-fixed paraffin-embedded tissue sections. Moreover, the RIBOMAP™ kit may be used in in situ hybridization with RNA probes (riboprobes) or DNA probes (oligoprobes). In one embodiment, the RIBOMAP™ kit is a reagent kit that comprises two prehybridization solutions, a hybridization solution, and a post-hybridization fixing solution. In a preferred embodiment, the RIBOMAP™ kit comprises: (a) an aqueous composition, comprising 0.15–1.5 M sodium chloride; 8–80 mM sodium phosphate dibasic; 2–20 mM sodium phosphate monobasic; 1–10 mM EDTA; 0.0125–0.125% first primary prehybridization detergent; 0.00375–0.0375% second primary prehybridization detergent; and 10–40% formalin; (b) an aqueous composition, comprising 0.1–1 N HCl; and (c) an aqueous composition, comprising 1×–5×SSPE; 10–50% dextran sulfate sodium salt, average molecular weight 10,000; 50–80% formamide; and 0.01–1% in situ hybridization detergent. In a most preferred embodiment, the RIBOMAP™ kit comprises: (a) an aqueous composition, comprising 0.3 M sodium chloride; 16 mM sodium phosphate dibasic; 4 mM sodium phosphate monobasic; 2 mM EDTA; 0.025% first primary prehybridization detergent; 0.0075% second primary prehybridization detergent; and 30% formalin; (b) an aqueous composition, comprising 0.3 N HCl; and (c) an aqueous composition, comprising 2×SSPE; 20% dextran sulfate sodium salt, average molecular weight 10,000; 80% formamide; and 0.05% in situ hybridization detergent.

The "CHIPMAP™" kit is designed for automated microarray hybridization, although it may also be used for manual methods of hybridization on a microarray. The CHIPMAP™ kit is a reagent kit that comprises a spreading enhancer solution, a blocking solution, a microarray hybridization solution, and a microarray cleaning solution. In a preferred embodiment, the CHIPMAP™ kit comprises: (a) an aqueous composition, comprising 4×–8×SSPE and 8–12% spreading enhancer detergent; (b) an aqueous composition, comprising phosphate buffer of 10–200 mM total salt concentration; 0.5–6% goat gamma globulins; 5–15% hydrolyzed casein; and 0.005–1% nonionic detergent; (c) an aqueous composition, comprising 2–6×SSPE; 17.5–22.5% dextran sulfate sodium salt, average molecule weight 10,000; and 10–50% formamide; and (d) an aqueous composition, comprising 0.1–5% microarray cleaning detergent. In a most preferred embodiment, the CHIPMAP™ kit comprises: (a) an aqueous composition, comprising 6×SSPE and 10% spreading enhancer detergent; (b) an aqueous composition, comprising 75 mM potassium phosphate; 25 mM sodium phosphate; 55 mM NaCl; 3% goat gamma globulins; 13.4% hydrolyzed casein; and 0.05% blocking detergent; (c) an aqueous composition, comprising 6×SSPE; 20% dextran sulfate sodium salt, average molecule weight 10,000; and 10% formamide; and (d) an aqueous composition, comprising 1% microarray cleaning detergent.

The terms "complementary" and "substantially complementary" refer to hybridization or base pairing between two nucleotides or nucleic acid molecules, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), and C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Substantial complementarity exists when an RNA or DNA strand will hybridize under selective hybridization conditions to its complement. Typically, selective hybridization will occur when there is at least about 65% complementarity over a stretch of at least 14 to 25 nucleotides, preferably at least about 75%, and more preferably at least about 90% complementary. See, for example, M. Kanehisa (1984) Nucleic Acids Res. 12:203.

"Double-stranded" nucleic acid refers to a hydrogen-bonded, helical array of nucleic acid that exists either between two separate strands, as with, for example, DNA, or within a single strand of "single-stranded" nucleic acid. In addition to the 100% complementary form of double-stranded nucleotides, the term double-stranded as used herein is also meant to refer to those forms which include such structural features as bulges and loops, which are described more fully in such biochemistry texts such as Stryer, Biochemistry, $3^{rd}$ ed. New York: Freeman and Co., 1988.

"Stringent hybridization" conditions will typically include salt concentrations of less than about 1M, more usually less than about 500 mM, and preferably less than about 200 mM. Hybridization temperatures can be as low as 5° C., but are typically greater than 22° C., more typically greater than about 30° C., and preferably in excess of about 37° C. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one parameter alone.

The term "specific hybridization" refers to the formation of hybrids between a probe polynucleotide (e.g., a polynucleotide of the invention which may include substitutions, deletion, and/or additions) and a specific target polynucleotide (e.g., an analyte polynucleotide) wherein the probe preferentially hybridizes to the specific target polynucleotide and substantially does not hybridize to polynucleotides consisting of sequences which are not substantially identical to the target polynucleotide. However, it will be recognized by those of skill in the art that the minimum length of a polynucleotide required for specific hybridization to a target polynucleotide will depend on several factors, for example: G/C content, positioning of mismatched bases (if any), degree of uniqueness of the sequence as compared to the population of target polynucleotides, and chemical nature of the polynucleotide (e.g., methylphosphonate backbone or phosphorothiolate), among others.

The reagents and kits of the invention may be used with any of several different automated instruments. Moreover, any of several automated instruments may be used in the methods of the invention. Such automated instruments include the models ES®, NEXES®, and BENCHMARK™ (all made by Ventana Medical Systems, Inc.), as described in U.S. Pat. No. 5,232,664 ("Liquid Dispenser"); U.S. Pat. No. 6,093,574 ("Automated Biological Reaction System"); and U.S. Pat. No. 6,045,759 ("Automated Biological Reaction System"); U.S. Provisional Patent Application No. 60/076,198, filed on Feb. 27, 1998 ("Automated Molecular Pathology Apparatus Having Independent Slide Heaters") and U.S. patent application Ser. No. 09/259,238, filed on Feb. 26, 1999 ("Automated Molecular Pathology Apparatus Having Independent Slide Heaters") each now U.S. Pat. No. 6,405,609; and Ser. No. 09/259,240, filed on Feb. 26, 1999 ("Automated Molecular Pathology Apparatus Having Independent Slide Heaters"), now U.S. Pat. No. 6,296,809; each of which is hereby incorporated by reference in its entirety.

The most preferred automated instrument to be used in the methods of the invention and with the reagents and kits of the invention is an instrument obtained from Ventana Medical Systems, Inc., Tucson, Ariz., having Product No. 750-200, and sold under the trademark DISCOVERY™. The DISCOVERY™ instrument is disclosed in U.S. Pat. No. 6,296,809, which is hereby incorporated by reference in its entirety.

The methods for automated in situ hybridization may be performed using either frozen, sectioned tissue or a cytospin preparation as the sample, neither of which requires deparaffinization prior to hybridization. A cytospin preparation may comprise, for example, tissue culture cells or cells from spinal fluid, urine, or other biological fluids. Alternatively, the methods for automated in situ hybridization of the invention may be performed using a paraffin-embedded tissue section, which must be deparaffinized prior to hybridization.

As described herein, certain tissue samples used with the methods, reagents, and kits of the invention may be embedded in a variety of inert material (e.g., paraffin, celloidin, agar, plastics, or acrylics) for preservation. Many of these inert materials are hydrophobic, while the reagents used for histological and cytological applications are predominantly hydrophilic. Therefore, the inert material may need to be removed from the tissue sample prior to use with the methods, reagents and kits of the invention. For example, the sample may be deparaffinized prior to use. Methods of deparaffinization that are appropriate for use in the methods of the invention are disclosed in U.S. patent application Ser. No. 09/721,096, filed Nov. 22, 2000, and Ser. No. 09/853,200, filed May 11, 2001, now U.S. Pat. No. 6,544,798, each of which is hereby incorporated by reference in its entirety.

Tissue fixation is one of the most important steps for a successful ISH assay. It has been found that the tissues should be fixed adequately in order to obtain an optimum signal to noise ratio. It is preferred that samples be treated with either neutral-buffered formalin (NBF) or paraformaldehyde (PFA) for a minimum of 24 hours at room temperature. As described herein, longer fixation times may result in better results. mRNA targets have been successfully recovered from tissue samples fixed for up to 168 hours at room temperature. Underfixed tissue samples (4–24 hours) produced lower signal and higher background staining compared to the samples fixed for 48–168 hours.

Fixed tissue may be processed for paraffin embedding and sectioning using standard protocols. Wrinkle-free paraffin section (5 mm) are placed onto appropriate glass slides, such as SUPERFROST™ PLUS slides (available from VWR International; Catalog No. 48311-703), after floating the sections on a water bath at a temperature of about 10° C. lower than the paraffin melting point. The slides are then air-dried prior to performing the ISH assays. To obtain maximum signal, the sections should be used as soon as possible after preparation. If tissue samples have been underfixed, signals may be enhanced and background staining reduced using RIBOPREP™, as described herein.

In preparing samples for ISH, paraffin tissue/cell sections may optionally be "re-fixed" with a formalin-based solution after deparaffinization, to prevent loss of nucleic acids and reduce background staining during ISH on the automated instrument. Over-fixation of tissue will decrease or even eliminate the detectable signal during ISH. It has been shown previously that an increased initial fixation time results in a higher signal in automated ISH. Thus, to compensate for under-fixation classically encountered in the histology settings, the present invention provides the additional step of performing fixation after deparaffinization, to produce increased intensity of signal obtained by ISH.

In one embodiment, re-fixation may be carried out using a 4% neutral buffered formalin (NBF) solution in water applied into a 200 µl layer of EZ PREP™ (Ventana Catalog No. 950-100) for 60 minutes at 37° C. This treatment was found to enhance the signal obtained by ISH (using an mPS2 gene probe on mouse stomach tissue) across samples originally fixed for 4, 8, 16, and 24 hours. In another embodiment, the re-fixation reaction is carried out using NBF in an SSPE-based buffer. These buffers have been demonstrated to reduce background staining and V-BLUE™ substrate precipitate, as described below. Thus, fixation may be performed on deparaffinized tissue samples using an NBF solution applied onto the glass slide (by manual or automated dispensing). For example, 100 µl of formalin solution (10% to 50%) may be diluted into a residual buffer layer of 200 µl of RIBOWASH™ and incubated at 37° C. for a limited time period, depending on the quality of the tissue sample.

Cell conditioning is an optional step, prior to the hybridization step, in the methods of automated in situ hybridization of the invention. The degree to which a sample is fixed will determine the amount of cell conditioning necessary prior to in situ hybridization. If the sample is lightly fixed, a mild cell conditioning procedure is recommended. However, if the sample is heavily fixed, a heavy cell conditioning procedure is recommended. For example, cell conditioning is usually not performed on frozen or poorly fixed tissue samples. Examples of appropriate cell conditioning procedures are described in U.S. patent application Ser. No. 09/800,689, filed Mar. 7, 2001, which is hereby incorporated by reference in its entirety.

Protease digestion is a further optional step, prior to the hybridization step, in the methods of automated in situ hybridization of the invention. For example, protease digestion may be accomplished by applying Protease I, II, or III to the sample (Ventana Medical Systems, Inc.; Catalog Nos. 760-2018, 760-2019, and 760-2020, respectively). Alternatively, one may use any of several proteases commonly used in in situ hybridization, such as proteinase K.

In another embodiment, an additional fixation step after the probe washing step may optionally be performed. This additional fixation step allows for incubation of the tissue sections with V-BLUE™ substrate (Ventana Product No. 760-062) for an extended time period. For instance, incubation has been performed for up to 10 hours without significantly increasing blue background staining. This allows for multiple applications of the substrate, resulting in increased signals.

Automated microarray hybridization may be performed using either commercially available microarrays or microarrays "spotted" by the user on commercially available slides. The methods for automated microarray hybridization may be used in procedures for analyzing known mutations in genetic diseases, genomic fingerprinting, linkage analysis, sequence determination, and mRNA population analysis, for example.

Nucleic acids used in the invention include oligonucleotides and cDNA molecules, or fragments thereof. An oligonucleotide is a single-stranded DNA or RNA molecule, typically prepared by synthetic means. cDNA, or fragments thereof, may be isolated or purchased from commercial sources. Those nucleic acids used in the invention are 15 to 2000 nucleotides in length, preferably from 70 to 1500 nucleotides, although nucleic acids of different length may be appropriate. Suitable oligonucleotides may be prepared by the phosphoramidite method described by Beaucage and Carruthers (1981) Tetrahedron Lett. 22:1859, or by the triester method according to Matteucci et al. (1981) J. Am. Chem. Soc. 103:3185, or by other chemical methods using either a commercial automated oligonucleotide synthesizer or Very Large Scale Immobilized Polymer Synthesis (VLSIPS™) technology.

In a microarray, nucleic acids (e.g., oligonucleotides or cDNA) are attached to a substantially solid support. In a preferred embodiment, the substantially solid support to which the nucleic acids are attached is a supporting film or glass substrate such as a microscope slide. The array of probe sequences may be fabricated on the substrate according to the pioneering techniques disclosed in U.S. Pat. No. 5,143,854 or International Publication No. WO 92/10092, which are hereby incorporated by reference. The combination of photolithographic and fabrication techniques may, for example, enable each probe sequence ("feature") to occupy a very small area ("site") on the support. In some embodiments, this feature site may be as small as a few microns or even a single molecule. For example, about $10^5$ to $10^6$ features may be fabricated in an area of only 12.8 mm$^2$. Companies presently manufacturing and marketing oligonucleotide or cDNA microarrays include Affymetrix, Santa Clara, Calif.; ClonTech, Palo Alto, Calif.; Corning, Inc., Corning, N.Y.; and Motorola, Inc., BioChip Systems Division, Northbrook, Ill.

The surface chemistry of the slides used for DNA printing has a very significant impact on the final outcome of the array. Coating methodologies that produce slides with low background fluorescence and uniform DNA bonding across the slide surface are very important. Ventana's DISCOVERY™ and CHIPMAP™ system, as described herein, are compatible with amino-silane, aldehyde, and polylysine-coated slides. Slides from the following sources have been evaluated on the system and found to perform satisfactorily:

1. Clontech Type I and II (Catalog Nos. 7880-1 and 7881);
2. Corning (Catalog No. 2549);
3. Sigma (Catalog No. P0425);
4. Telechem (Catalog No. CSS 100);
5. NEN (Catalog No. MPS620).

Due to the increased kinetics resulting from mixing and washing on the DISCOVERY™ instrument, the bonding of DNA to the glass substrate is critical if consistent results are to be obtained. It is essential that the DNA be tightly bound to the surface following printing. If post-printing bonding is omitted, the risk of washing off significant amounts of spotted probe is high.

It is strongly recommended to follow the slide manufacturer's suggested baking/drying and cross-linking procedure prior to running the arrays on the DISCOVERY™. It is also recommended that all arrays be scanned prior to running on the DISCOVERY™ system. This allows the identification of arrays having printing, background, or damage issues prior to being run. In addition, by comparing spots containing labeled probe pre- and post-hybridization, it is possible to identify arrays that produce weak signal due to poor cross-linking and subsequent loss of probe DNA.

Multiple steps are required for practicing the method for automated microarray hybridization of the invention. The microarrays are placed into the instrument, such as the DISCOVERY™ instrument, and exposed to the conditions described herein. The solutions described herein are applied to the microarrays within the instrument. For example, the solutions for use in prehybridization, hybridization, and washing are contained in and dispensed from liquid dispensers (e.g., "user-fillable" dispensers), such as those described in U.S. Pat. Nos. 6,045,759 and 6,192,945, each of which is hereby incorporated by reference in its entirety. The type of dispenser used for the solutions of the invention (whether for in situ hybridization or microarray hybridization) is not critical. The microarrays are treated under the conditions described herein. Unless otherwise indicated, all reagents were obtained from Ventana Medical Systems, Inc., and all reactions processed on slides were performed under a film of LIQUID COVERSLIP™ to prevent evaporative loss of water during processing.

Detergents have been used in hybridization solutions by investigators to reduce non-specific binding of labeled probe to spotted nucleic acid on glass slides during manual hybridization. It is generally believed that such detergents increase the stringency of the reaction, thereby resulting in reduced non-specific binding. In conjunction with previous efforts to hybridize nucleic acid arrays on the DISCOVERY™, a detergent was incorporated into the hybridization buffer. While this had a positive effect on the hybridization reaction, it also decreased coverage during long incubation periods (e.g., 4–6 hours).

Attempts to eliminate these detrimental effects by altering salt (2×–12×SSPE/SSC) or detergent concentrations (1–20%), as well as substituting different detergents (for example, TWEEN® 80 (nonionic detergent comprising polyoxyethylenesorbitan monooleate; available from Sigma-Aldrich, Inc., St. Louis, Mo., Product No. P8074), NP-40 (nonionic detergent comprising polyglycol ether surfactants; available from Sigma-Aldrich, Inc., St. Louis, Mo., Product No. NP-40), or BRIJ® 35 nonionic detergent comprising polyoxyethylene(23) lauryl ether, having a molecular formula of $C_{12}H_{25}(OCH_2CH_2)_nOH$, n~23; available from Sigma-Aldrich, Inc., St. Louis, Mo., Product No. 858366)), in the microarray hybridization solution were not successful. However, if the positive effect exerted by the detergent was not due to simple prevention of non-specific binding through a traditional stringency effect, but rather to improved hydration of the spotted nucleic acids or similar mechanism, then treating the slide with the detergent prior to hybridization might provide the same benefit. Thus, the use of a solution containing detergent was considered for use in a prehybridization step.

"Spreading enhancer solution" (SES), described herein, is one such solution that was found to reduce non-specific hybridization and ensure initial slide surface coverage. In one embodiment, the slide is treated with SES prior to hybridization. Pre-treatment with the solution decreases background binding of probe to spotted DNA and thereby increases the signal-to-noise ratio. In a preferred method of using SES, two drops of the solution (200 µl; resulting in a actual on-slide concentration of approximately 3.6×SSPE, and 4% spreading enhancer detergent) are dispensed onto the slide and incubated for ten minutes at 70° C. This treatment prior to hybridization increases the wetability of the slide surface, improving coverage by aqueous solutions during subsequent steps and increasing accessibility of labeled target DNA/RNA to nucleic acids probes bound to the slide surface. In addition, treating the slide with SES prior to hybridization lowers the binding of labeled target DNA/RNA to negative (non-homologous) nucleic acids spotted on the slide surface, thus improving the signal-to-noise ratio obtained during hybridization.

Traditionally, high concentrations of protein (e.g., BSA, casein, or powdered milk) have been utilized to block nonspecific binding of reagents used in immunohistochemistry (IHC), ISH, and membrane blotting. The present invention provides an improved method for prehybridization of slides that permits increased coverage of the slide during extended incubations. For use in the described assays, two drops (200 µl) of blocking solution are applied to the slide, followed by a 30 minute incubation at room temperature. The proteins contained in blocking solution coat the slide surface through nonspecific charge and hydrophobic interactions to reduce later nonspecific binding of labeled target DNA/RNA to the slide surface during hybridization. Due to the nonspecific nature of these interactions, the increased kinetic energy at elevated temperatures reduces the efficiency of the blocking. Therefore, treatment with blocking solution to reduce the nonspecific binding of the labeled DNA/RNA target to the slide is carried out at ambient temperatures by disabling the individual slide heaters on the automated instrument during this pretreatment. Following a 30 minute incubation, the slide is rinsed to remove any unbound protein prior to hybridization.

Although the original intent of this pretreatment was simply to reduce the nonspecific binding of labeled target DNA/RNA to the slide, it was noted during development of this solution that slides treated with blocking solution retained significantly better coverage of the slide surface by the hybridization buffer at extended hybridization incubations (e.g., up to 16 hours). In addition, when compared to the standard 5% BSA solution commonly used to block nonspecific binding, slide coverage was better on the slides treated with blocking solution. Uniform coverage is essential for consistent array hybridization, therefore, treatment of the slide with blocking solution prior to hybridization has been incorporated into the standard method for automated microarray hybridization of the invention.

In standard hybridization assays, nucleic acid probes are hybridized with a target sequence in a solution such that nonspecific binding is inhibited and specific binding is maintained. The choice of hybridization buffer can be a critical factor in the overall sensitivity of the assay. Several different hybridization methodologies defined for manual hybridization are known in the art. For instance, commercially available solutions such as EXPRESS-HYB™ (Clontech; Palo Alto, Calif.) may be useful. In certain embodiments, the ULTRARRAY™ hybridization and wash reagents (Ambion; Austin, Tex.) are useful (e.g., with the SLIDEHYB™ system; Ambion; Austin, Tex.). An initial denaturation step is typically performed to allow for optimal interaction between probe (or target nucleic acid) and the nucleic acids forming the microarray.

Typically, prior to hybridization of the nucleic acid probes on the microarray to the target nucleic acid, the buffer is removed and replaced with a solution containing the target nucleic acid (e.g., hydrolyzed RNA) in hybridization buffer and mixed well. The target nucleic acid and the oligonucleotide probes fixed to the slide are then preferably incubated for 30 minutes to 12 hours at 42–60° C. The hybridization buffer is then removed.

According to the method for automated microarray hybridization of the invention, a sufficient quantity of hybridization solution containing the labeled target solution is added to the surface of the microarray. Hybridization reactions are typically performed in a hybridization solution containing between 200 ng to 20 µg of labeled target nucleic acid. The dextran sulfate utilized in the hybridization solution of the invention is low molecular weight dextran sulfate, approx. 10,000 avg. mol. wt., as described in co-owned U.S. patent application Ser. No. 09/772,123, filed Jan. 29, 2001, which is hereby incorporated by reference in its entirety.

Following hybridization, the microarray is typically washed under conditions of high or low stringency, depending on the calculated binding properties of the target:probe hybrid. For example, in the series of stringency washes, the slide is typically washed one to three times with changes of 0.05× to 1× wash solution (e.g., RIBOWASH™), typically at temperatures between 37–42° C. for between 2 and 6 minutes each. In one embodiment, the first wash may be in 1× wash solution, the second in 0.5× wash solution, and the third in 0.05× wash solution. Alternatively, a wash may occur in 0.25× wash solution. However, it must be emphasized that washing conditions (e.g., salt concentrations, temperatures, and incubation times) will vary depending on the probe and target used in the method.

Following hybridization of a probe to a microarray and prior to analysis of the hybridization patterns, one may optionally remove the LIQUID COVERSLIP™ from the slide. The LIQUID COVERSLIP™ interferes with the analysis in that it causes autofluorescence. It was known from immunohistochemistry (IHC) studies that DAWN® dishwashing detergent was an effective cleaning agent. Initially, slides were cleaned using 5% DAWN® in 2×SSPE followed by 1×SSPE and EtOH rinses. This procedure often resulted in a soapy film remaining on the array, resulting in autofluorescence. Other cleaning solutions have been tested (e.g., sodium dodecyl sulfate (SDS) alone or in combination with DAWN®) in an effort to improve and simplify the process with little success.

Studies were performed, however, that indicated detergent levels of 0.01% to 0.5% were sufficient and reduced the incidence of autofluorescence relative to that observed at the 5% level. It was also demonstrated that heating the microarray cleaning solution to approximately 40° C. significantly increased its efficiency (i.e., by reducing the number of washes required). However, significant variability remained in the consistency of the end-result. The procedure was subsequently automated in an attempt to eliminate this variability. Initial studies demonstrated that a 0.1% solution of microarray cleaning detergent in deionized water followed by a wash in deionized water allowed for automation of the process and improved consistency of cleaning.

In adapting this procedure to the DISCOVERY™ system, a microarray cleaning solution is placed into a dispenser, which then dispenses microarray cleaning solution into Reaction Buffer (Ventana Catalog No. 760-105) in an approximate ratio of 1:10 (microarray cleaning solution:Reaction Buffer), followed by application to the slide for two minutes at 37° C. This sequence of events is repeated three times, followed by two final washes in Reaction Buffer to remove the remaining microarray cleaning detergent. This procedure allows for removal of the LIQUID COVERSLIP™, reduces autofluorescence, and provides consistency of the signal over previously utilized manual procedures.

When removing the slides from the instrument, the back of the slide is typically wiped to remove residual LIQUID COVERSLIP™, and the slides are placed upside down into Reaction Buffer so the coverslip from the barcode will not seep down the slide. The slide is then rinsed twice in Reaction Buffer and then twice in deionized water, after which the slide is dried. Preferably, the slide is dried with a nitrogen gun. Alternatively, however, the slide may be dried by centrifugation, in which case it should first be rinsed twice in molecular grade EtOH; isopropyl alcohol coats the slides with a bright blue film that raises the background and conceals the signal.

The following examples are presented for illustrative purposes only and are not intended, nor should they be construed, as limiting the invention in any way. Those skilled in the art will recognize that variations on the following can be made without exceeding the spirit or scope of the invention.

EXAMPLE 1

Automated In situ Hybridization with a Riboprobe

A tissue sample is fixed, either in neutral-buffered formalin (NBF) or paraformaldehyde (PFA), embedded in paraffin and cut into 5 mm sections. A paraffin section is then placed onto a microscope slide and stained for one or more targets using ISH techniques. Traditional ISH protocols are very time consuming and technically very involved. However, once the slide is prepared, the remaining ISH protocol is automated on the DISCOVERY™ system.

DISCOVERY™ ISH protocols include deparaffinization, various pretreatment steps, hybridization, post-hybridization stringency washes, and chromogenic signal detection. The RIBOMAP™ kit supplies the reagents for optimal pretreatment steps. Detection is performed using biotin-labeled antibody recognition of DIG molecules, followed by streptavidin-alkaline phosphatase (SA-AP) binding to the antibody. Colorimetric detection using the V-BLUE™ substrate (Ventana Product No. 760-062) is catalyzed by the alkaline phosphatase enzyme. The slides are then counterstained and coverslipped for microscopic evaluation.

A preferred method for mRNA ISH is summarized as follows:

A. Tissue Preparation: collection, NBF/PFA fixation, processing using a tissue processor, and sectioning using a microtome;

B. DISCOVERY™ ISH Protocol: baking, deparaffinization; pretreatment using RIBOPREP™, RIBOCLEAR™, RIBOCC™, and protease digestion using Protease I, II, or III (Ventana Medical Systems, Inc.; Catalog Nos. 760-2018, 760-2019, and 760-2020, respectively); hybridization using DIG-labeled riboprobe and RIBOHYBE™; stringency washes using serial dilutions of RIBOWASH™; post-treatment with RIBOFIX™; signal detection by incubation of the sample with a primary antibody, incubation with a biotin-labeled anti-DIG antibody and antibody diluent, and use of the enhanced V-BLUE™ kit (Ventana Medical Systems, Inc.) (SA-AP conjugate incubation and V-BLUE™ substrate incubation); and counterstaining. The samples are then analyzed microscopically.

The riboprobe is prepared by labeling the riboprobe with digoxigenin (DIG)-UTP using Roche DIG RNA Labeling Kit (SP6/T7)(Catalog No. 1175025), and T3 RNA Polymerase (Roche Catalog No. 1031163, 1000 U; or Catalog No. 1011171, 5000 U). Quantitative analysis of DIG-labeled riboprobes is performed using the Roche DIG Nucleic Acid Detection Kit (Catalog No. 1175041) and Roche DIG Wash and Block Buffer Set (Catalog No. 1585762). Antisense and sense probes are prepared according to the manufacturer's protocol (available at www.roche.com).

The probe is diluted to a final concentration of 100 ng/ml in RIBOHYBE™, and 100 µl are used per slide. The optimal probe concentration should be determined for each probe. The probe is applied to the slide using the "Manual Application Wet" step in the DISCOVERY™ protocol. The probe is applied manually and gently mixed with the hybridization buffer without forming bubbles.

Anti-DIG antibody (clone DI-22; Sigma Catalog No. B7405) is diluted 1:500 in Ventana Antibody Diluent (Catalog No. 251-018) and filtered into a Ventana User-Fillable "Antibody" dispenser (Catalog No. 770-001 to 770-050). Biotin-labeled anti-DIG antibodies from other sources, such as Jackson ImmunoResearch, diluted 1:4000, may also be used (www.jacksonimmuno.com).

Controls are also used, as follows: (1) probe control—sense probe; (2) tissue control—a control tissue known to express the target gene. The use of controls ensures the quality of the results obtained. It is preferable that RNA preservation in the tissues be confirmed by visualizing highly expressed genes, such as 28S rRNA (Cleveland et al. (1980) Cell 20:95) or beta-actin (Toshii et al. J. Histochem Cytochem 43:321). Following establishment of ISH protocols for visualizing the control targets, the protocol may be used for experimental targets.

The following represents the recommended protocol for using the DISCOVERY™ ISH system.

1. Baking: pre-programmed for paraffin sections.
2. Deparaffinization: pre-programmed.
3. Pretreatment:
   a. RIBOPREP™: 30 min, 37° C.;
   b. RIBOCLEAR™: 10 min, 37° C.;
   c. cell conditioning using RIBOCC™: "Mild CC1" setting;
   d. enzyme digestion using Protease II: 2 min, 37° C.
4. Hybridization:
   a. probe application: "Manual Application Wet";
   b. denaturation: 10 min, 70° C.;
   c. hybridization using RIBOHYBE™: 2 hours at 60° C. for highly expressed mRNA; 6 hours at 60° C. for "medium" expressed mRNA;
   d. stringency washes: two washes with RIBOWASH™: 6 min. at 65° C.;
   e. posttreatment: RIBOFIX™ for 20 min at 37° C.;
   f. signal detection:
      i. anti-DIG antibody: 20 min, 37° C.;
      ii. V-BLUE™ Enhanced Detection Kit (Ventana Medical Systems, Inc.; program automatically applies Enhanced SA-AP, Enhanced Enhancer, Enhanced NBT and Enhanced BCIP of the kit): for highly expressed mRNA, substrate incubation is for 2 hours; for "medium" expressed mRNA, substrate incubation is for 5 hours.

V-BLUE™ reaction time should be adjusted according to the user's preferences for the signal to noise balance. The signal may be developed for up to several hours, but the background may continue to increase. An optimum time for incubation for ISH is typically 2 hours for highly expressed genes.

EXAMPLE 2

Automated In situ Hybridization with an Oligoprobe

Formalin-fixed, paraffin-embedded sections of the mouse oviduct are processed in pretreatment steps with the following RIBOMAP™ reagents: RIBOPREP™, RIBOCLEAR™, and RIBOCC™. In addition, Protease, I, II, or III (Ventana Medical Systems, Inc.; Catalog Nos. 760-2018, 760-2019, and 760-2020, respectively) may be used in the protocol.

Next, the tissue sections are hybridized with DIG-labeled estrogen receptor a (ERα) sense or antisense oligoprobe using the hybridization buffer of the CHIPMAP™ system, CHIPHYBE™ (Ventana Medical Systems). As a positive control for RNA preservation in the tissue sections, parallel tissue sections are hybridized with DIG-labeled 28S rRNA antisense oligoprobe (Yoshii et al. (1995) J. Histochem. Cytochem. 43: 321). Oligoprobes are synthesized by conventional methods, and labeled with a tailing kit made by Roche Diagnostics (Indianapolis, Ind.).

After hybridization for five hours, the slides are washed in one to three stringency washes of 1×–0.05× RIBOWASH™ each. Typically, there will be three stringency washes, each with a progressively more dilute solution of RIBOWASH™. For example, the first stringency wash is in 1× RIBOWASH™, the second in 0.5× RIBOWASH™, and the third in 0.05× RIBOWASH™. Each wash is performed at temperatures approximately ten degrees higher than the temperature at which hybridization is performed (for example, between 47–60° C.) for between about 2 and about 30 minutes each.

Next, the samples are treated with RIBOFIX™ reagent, and signals are detected using anti-DIG alkaline phosphatase conjugated secondary antibody (Sigma, 1:500), incubated for 20 minutes, and an alkaline phosphatase signal detection system (V-BLUE™ detection kit). All preliminary treatment, hybridization, and washing steps are performed on the DISCOVERY™ instrument (Ventana Medical Systems). Finally, samples are analyzed microscopically.

As displayed in FIG. 1, sections that were not exposed to probe show no significant signal. However, sections that were exposed to the 28S rRNA antisense oligoprobe displayed abundant signal, demonstrating the preservation of RNA in the mouse oviduct sections. Furthermore, the ERα antisense oligoprobe showed precise localization of ERα mRNA in the mouse oviduct tissue sections. Meanwhile, the ERα sense oligoprobe showed no significant signal, as expected. The localization of ERα mRNA in the oviduct was verified by comparison to published estrogen receptor immunohistochemical data (Cooke et al. (1997) Proc. Natl. Acad. Sci. USA 94:6535).

EXAMPLE 3

Protocol for In situ Hybridization Using the DISCOVERY™

DISCOVERY™ ISH protocols may be created on DISCOVERY™ ISH software on the computer unit of the DISCOVERY™ System, as follows:
1. Open NEXES® software.
2. To create a protocol, click on the "Protocols" button on the main screen. A window appears on the screen with "Create/Edit Protocol" and "Delete Protocol". The user clicks on "Create/Edit Protocol" to open the "NEXES® Protocol Editor-DISCOVERY™ Staining Module" window.
3. Select the "Research ISH Blue Plus" procedure under the "Procedure" filed.

To set the pretreatment steps:
1. Click on the check box next to "Deparaffinization".
2. Click on the check box next to "Fixative". New fields appear on the screen. In the "Low Temperature" field, select "37 Deg C.". In the "Fixative" field, select "RIBOPREP™". Under the "Plus Incubation Time" select "20 minutes".
3. Click on the check box next to "Pretreatment #1". Two new check boxes appear on the screen. Click on the box next to "Use EZ Buffer for PT1". Two new check boxes appear on the screen. Click on the box next to "Heat slides for PT1-EZ". Three new fields appear on the screen. Under the "Low Temperature" field, select "37 Deg C.". Under "Pretreatment" select "RIBOCLEAR™". Under "Incubation Time" select "10 minutes".
4. Click on the check box next to "Cell Conditioning". Two new check boxes appear on the screen. Click on the check box next to "Conditioner #1". One new check box appears on the screen, and the user clicks on "Mild CC1". A new check box appears on the screen for "Standard CC1" (the user does not click on this box).
5. Click on the box next to "Pre-treatment #2. Two new check boxes appear on the screen. Click on the box next to "Use Reaction Buffer for PT2". Two new check boxes appear on the screen. Click on the box next to "Heat Slides for PT2-RB". Three new fields appear on the screen. Under the "Low Temperature" select "37 Deg C.". Under "Enzyme" select "PROTEASE 2". Under "Incubation Time" select "2 Minutes".

To select hybridization and stringency wash conditions:
1. Click on the check box next to "Probe". Two new check boxes appear on the screen above "Probe" and four new fields appear. Click on the check box next to "Titration". The "Probe Auto Dispense" will disappear from the screen and two new check boxes appear beneath "Titration". Click on the box next to "Manual Application Wet".
2. The "Probe" panel on the screen is for setting the denaturation and hybridization conditions. Under the "High Temperature" filed for "Denaturation", select "65 Deg C." and under the "Denaturation Incubation Time" field select "6 Minutes". Under the "Low Temperature" filed for the "Hybridization" select "60 Deg C." and under the "Hybridization Incubation Time" field select with "2 Hours" (high mRNA expression) or "6 Hours" (medium mRNA expression).
3. Click on the check box next to "Stringency Wash #1". New field "Stringency Wash" and a check box next to "High Temp Stringency #1" will appear on the screen. Under the "Stringency Wash" field select "0.1×SSC". Ignore the check box next to "High Temperature", and under the "Low Temperature" window select "60 Deg C." and under the "Incubation Time" field select "6 Minutes".
4. Repeat step 3 above for "Stringency Wash #2".
5. Click on the box next to "Post Fixative", and two fields appear on the screen. Under Fixative, select "RIBOFIX™" and under "Incubation Time" select "20 Minutes".

To set antibody incubation and V-BLUE™ Enhanced Kit Conditions:

1. Click on the box next to "Antibody". Two new check boxes appear on the screen. Click on the box next to "Antibody Auto Dispense". Two new check boxes appear on the screen. Click on the box next to "Standard Ab Incubation". Two new fields appear on the screen. Under the "Antibody" field, select the "ANTIBODY #(corresponding to the number on the dispenser containing your anti-DIG antibody)". Under the "Plus Incubation Time" select "20 Minutes".
2. In the "Substrate" field without the check box, under "Long Incubation Time" select "2 Hours" (high mRNA expression) or "5 Hours" (medium mRNA expression).

To save the protocol:

1. Click on the "Save As" button. Fields appear for a name and protocol number. Type in a name for the protocol and select a number in the appropriate boxes. Click on the "Close" button again and the protocol will be saved.

To prepare labels and load slides:

1. From the tool bar on the bottom of the main screen, click the barcode symbol. Click on the "Protocols" button. Highlight the protocol number and name desired in the "Select DISCOVERY™" protocols field. Click on the "Add>>" button once for each protocol barcode label you want to print. Click on the "Close/Print" button. Enter any additional information you want to appear on the label in the "User Prompt" fields. Click the "Print" button. When the last barcode has been printed, click on the "Exit" button.
2. Place the bar code(s) on the slide(s), load them carefully onto the instrument, close the door and click on the "Run" button. Click on the "Reagents/Reagent Tray Loaded" box and "Reagents Caps Removed" box. Enter the number of slides loaded and click on "Start Run".

Table 1 lists potential problems that may arise when using the DISCOVERY™ instrument for ISH and possible solutions.

TABLE 1

"Trouble-Shooting" Guide

| Problem | Possible Cause | Next Step |
|---|---|---|
| No Signal | 1. Poorly prepared or degraded probes<br>2. Inadequate protease digestion<br>3. Low gene expression | 1. Prepare fresh probes correctly.<br>2. Use stronger protease or increase digestion time (may cause higher background).<br>3. Test the probes and protocols on tissues known for high expression. |
| Weak Signal and Low Background | 1. Low probe concentration<br>2. Short substrate incubation period | 1. Increase probe concentration.<br>2. Extend substrate incubation. |
| Weak Signal and High Background | Poor tissue fixation | Extend RIBOPREP ™ incubation time or re-collect samples and fix for longer time. |
| Signal too strong and low background | High probe concentration | Use less probe or shorten the V-BLUE ™ substrate incubation time. |
| Strong signal and high background | 1. Over-protease digestion<br>2. High probe concentration | 1. Use weaker protease or shorten protease digestion time (if digested longer than 2 minutes). |

TABLE 1-continued

"Trouble-Shooting" Guide

| Problem | Possible Cause | Next Step |
|---|---|---|
| | 3. High antibody concentration<br>4. Long RIBOFIX ™ incubation | 2. Use lower probe concentration.<br>3. Use lower antibody concentration.<br>4. Shorten RIBOFIX ™ incubation. |
| Poor tissue morphology | 1. Poorly fixed tissues<br>2. Over-protease digestion<br>3. Poorly cut sections | 1. Extend RIBOPREP ™ incubation period or fix new samples for longer period and process correctly.<br>2. Use weaker protease or shorten protease digestion time (if digested for longer than 2 minutes).<br>3. Cut sections carefully with fresh blades. |

EXAMPLE 4

Preparation of CHIPPREP™ 1

The following equipment and reagents are utilized:

1. Clean, appropriately sized mixing container;
2. 0.2 μm filter system or 0.2 μm filter and appropriate pumping equipment;
3. mixing equipment appropriate to the size of the preparation;
4. appropriately sized Class A graduated cylinders;
5. electronic balance and weighing supplies;
6. clean, appropriately sized storage container;
7. deionized water;
8. 20×SSPE (Sigma P/N S8140);
9. TWEEN® 20 (Sigma P/N P7949).

The following steps are performed:

1. a clean, suitably sized mixing container is labeled "CHIPPREP™ 1 In-Process Bulk," dated and initialed;
2. the container type and size is recorded;
3. the volume of deionized water to be added is calculated to 80% of the final batch volume of CHIPPREP™ 1, as follows: batch volume×0.8=total volume of deionized water to add to container;
4. vigorous mixing is performed using a magnetic stir bar;
5. the required volume of 20×SSPE is added such that the final concentration is 6×, as follows: final batch volume divided by 20×6=volume of 20×SSPE to add;
6. add TWEEN® 20 (Sigma P/N P7949) to a final concentration of 10%, as follows: final batch volume× 0.1=volume of TWEEN® 20 to add;
7. mix for at least 20 minutes;
8. add deionized water to bring solution to final batch volume;
9. mix for at least 30 minutes;
10. label the storage container of a 0.2 μm filter unit with a label as "CHIPPREP™ 1 Final Bulk", L/N, date and initial; record the type and size of storage container;
11. filter the solution through a 0.45 μm filter unit;
12. filter the solution through the 0.2 μm filter attached to the labeled storage container;
13. store the bulk solution of CHIPPREP™ 1 at room temperature.

EXAMPLE 5

Preparation and Use of CHIPPREP™ 2

In one embodiment, CHIPPREP™ 2 comprises phosphate buffer of any total salt concentration; proteinaceous material (e.g., gamma globulins, casein, or any other protein suitable for blocking nonspecific binding); and nonionic detergent. In a preferred embodiment, CHIPPREP™ 2 comprises phosphate buffer of 10–200 mM total salt concentration; 0.5–6% goat gamma globulins; 5–15% hydrolyzed casein; and 0.005–1% nonionic detergent. In a most preferred embodiment, CHIPPREP™ 2 comprises 75 mM potassium phosphate; 25 mM sodium phosphate; 55 mM NaCl; 3% goat gamma globulins; 13.4% hydrolyzed casein; and 0.05% BRIJ® 35.

For use in the described assays, two drops (200 µl) are applied to the slide followed by a 30-minute incubation at room temperature. The proteins contained in CHIPPREP™ 2 coat the slide surface through nonspecific charge and hydrophobic interactions to reduce later nonspecific binding of labeled target DNA/RNA to the slide surface during hybridization. Due to the nonspecific nature of these interactions, the increased kinetic energy at elevated temperatures reduces the efficiency of the blocking. Therefore, treatment with CHIPPREP™ 2 to reduce the nonspecific binding of the labeled DNA/RNA target to the slide is carried out at ambient temperatures by disabling the individual slide heaters on the automated instrument during this pretreatment. Following a 30 minute incubation, the slide is rinsed to remove any unbound protein prior to hybridization.

Although the original intent of this pretreatment was simply to reduce the non-specific binding of labeled target DNA/RNA to the slide, it was noted during development of this solution that slides treated with CHIPPREP™ 2 retained significantly better coverage of the slide surface by the hybridization buffer at extended hybridization incubations (e.g., up to 16 hours). In addition, when compared to the standard 5% BSA solution commonly used to block nonspecific binding, slide coverage was better on the CHIPPREP™ 2-treated slides. Uniform coverage is essential for consistent array hybridization. Therefore, treatment of the slide with CHIPPREP™ 2 prior to hybridization has been incorporated into the standard microarray protocol on the DISCOVERY™.

EXAMPLE 6

Preparation of CHIPHYBE™

CHIPHYBE™ solution preferably consists of 6×SSPE; 20% dextran sulfate sodium salt, average molecular weight 10,000; and 10% formamide. Deionized formamide may be obtained from Sigma Corp. (Product No. F9037), as can 20×SSPE (Sigma Product No. S8140) and dextran sulfate sodium salt, average molecular weight 10,000 (Sigma Product No. D6924). The required equipment for preparing CHIPHYBE™ is as follows:

1. clean, appropriately sized mixing container;
2. 0.2 µm filter system or 0.2 µm filter and appropriate pumping equipment;
3. mixing equipment appropriate to the size of the preparation;
4. appropriately sized Class A graduated cylinders;
5. electronic balance and weighing supplies;
6. clean, appropriately sized storage container.

Formamide, 20×SSPE and dextran sulfate are added to deionized water in the appropriate volumes to attain the correct final concentrations. For instance, if the batch volume is 1 L, then to 400 ml deionized water is added formamide to 10% final volume (i.e., 100 ml of Sigma Product No. F9037), 20×SSPE to a final concentration of 6× (i.e., 300 ml of Sigma Product No. S8140), and 200 g of dextran sulfate (i.e., Sigma Product No. D-6924). The final volume is then brought to 1 L by adding deionized water with mixing. Vigorous mixing is performed during addition of these constituents. The solution is then packaged into liquid containers compatible with the DISCOVERY™ automated hybridization system.

EXAMPLE 7

CHIPMAP™ Kit

The DISCOVERY™ CHIPMAP™ kit provides reagents for hybridization of a labeled target to a DNA microarray using the Ventana DISCOVERY™ instrument.

As described above, the ability to spread buffer uniformly over the entire surface of an array is critical for automation of the hybridization reaction on a glass slide. The pretreatment reagents provided in the CHIPMAP™ kit prepare the surface of the array and, in combination with the specially formulated hybridization buffer, ensure uniform coverage of the labeled target array surface. In addition, these reagents have been formulated so that their combined use provides a reduction of nonspecific binding, resulting in improved signal. Automation of the hybridization process on the DISCOVERY™ system reduces slide to slide variation, decreases time of hybridization, and increases the signal to noise ratio.

In one embodiment, at least one of each of the following components is included in the kit:

1. CHIPPREP™ 1 (spreading enhancer; storage at ambient room temperature);
2. CHIPPREP™ 2 (spreading enhancer and blocking solution, storage at room temperature until opened, then 2–8° C.);
3. CHIPHYBE™ (hybridization buffer, storage at room temperature);
4. CHIPCLEAN™ (array cleaning solution);
5. (the kit may optionally contain) user-fillable dispensers
6. package insert containing instructions for use.

Additional reagents required but not necessarily included with the kit:

1. LCS™ (Ventana Catalog No. 650-010);
2. EZ PREP™ (Ventana Catalog No. 950-100);
3. RIBOWASH™ (Ventana Catalog No. 760-105);
4. Reaction Buffer (Ventana Catalog No. 760-105).

Others materials required but not supplied by Ventana Medical Systems, Inc.:

1. microarray;
2. labeled target;
3. centrifuge or nitrogen gun.

CHIPPREP™ 1, CHIPPREP™ 2, and CHIPCLEAN™ are transferred to Ventana user-fillable dispensers. Before transferring the contents, the user should read the instructions provided on the package insert accompanying the dispenser. Other instructions are provided below.

EXAMPLE 8

Target Synthesis and Labeling for Automated Microarray Hybridization

Proper preparation and labeling of the nucleic acid target is essential for consistent hybridization results. Reverse transcription using a nucleotide triphosphate (dNTP) mix, which includes the fluorescently-tagged nucleotide, is a common method of target labeling. Either total RNA or polyA RNA (mRNA) may be used as a starting material for reverse transcription.

The Ventana DISCOVERY™ system has been evaluated for use with both directly labeled target (e.g., incorporation of cyanine nucleotides, such as cy3-dUTP or cy5-dUTP) and indirectly labeled target (e.g., labeling by incorporation of aminoallyl-dUTP followed by the coupling of the monofunctional, N-hydroxysuccinimide-activated fluorescent dyes cy3 or cy5). Regardless of the labeling procedure chosen, it is recommended that 0.5–2.0 mg of labeled target be applied to each array as a starting point on the DISCOVERY™ hybridization system.

Two target-labeling protocols are recommended. The amplification protocol is used when the amount of RNA is limited and requires amplification. The non-amplification protocol is utilized when the amount of RNA available is not a limiting factor. In the amplification protocol, total RNA is converted into double stranded cDNA (dscDNA). dscDNA is then subjected to in vitro transcription (i.e., amplification). The in vitro transcribed material is then converted into single-stranded DNA (ssDNA) labeled probe. Target quality is then analyzed. On the other hand, in the non-amplification protocol, total RNA is converted directly into ssDNA labeled probe, without an intervening amplification step, and the quality of the target population is determined.

At the step where the in vitro transcribed material or total RNA is converted into labeled ssDNA (step 3 in the amplification protocol below), the same labeling protocol is used. Either 4 μg of cRNA or 20 μg of total RNA is used as starting material, with all other amounts (including the amount of random hexamer primers) remaining the same.

An example of an appropriate target synthesis and labeling protocol follows.

Step 1: Preparation of Double-stranded cDNA a. First strand cDNA synthesis using polydT primers
  i. Mix 10 μl of total RNA (5–10 μg) with 1 μl of T7-(T)24 primer (100 pmol/ul); Primer sequence (custom primers): GGCCAGTGAATTGTAATACGACTCAC-TATAGGGAGGCGG-T(24) (SEQ ID NO:1).
  ii. Heat at 70° C. for 10 minutes; put on ice.
  iii. Add, on ice, to RNA/primer mix:
    1) 4 μl 5× first strand buffer;
    2) 2 μl 0.1 mM DTT;
    3) 1 μl 10 mM dNTP.
  iv. Incubate at 37° C. for two minutes.
  v. Add 2 μl of SuperScript II (SSII).
  vi. Incubate at 37° C. for one hour, and place on ice.
  (Note: first stand buffer, 0.1 mM DTT and SSII are available as a kit (Gibco Catalog No. 18064-014))
b. Second strand cDNA synthesis
  i. Set PCR machine or water bath to 16° C.
  ii. Add the following to the first strand tube:
    1) 91 μl of Gibco water (Gibco Catalog No. 10977)
    2) 30 μl 5× $2^{nd}$ strand buffer (Gibco Catalog No. 10812014)
    3) 3 μl 10 mM dNTP mix (Gibco Catalog No. 18427-013)
    4) 1 μl E. coli ligase (Gibco Catalog No. 18052-019)
    5) 4 μl E. coli DNA polymerase I (Gibco Catalog No. 18010-017)
    6) 1 μl of E. coli RNase H (Gibco Catalog No. 18021-014)
  iii. Incubate at 16° C. for two hours.
  iv. Terminate the reaction by adding 10 μl of 0.5 M EDTA and place tubes on ice.
c. Clean-up of dscDNA
  i. Add to the dscDNA reaction (150 μl) an equal volume of phenol:chloroform:isoamylalcohol (25:24:1) (Gibco Catalog No. 15593-031) and vortex for 30 seconds.
  ii. Spin phase lock gel tubes (Eppendorf 5 prime Catalog No. 32007953) for one minute at maximum speed.
  iii. Add the cDNA plus phenol mix to the spin phase lock gel tubes and spin two minutes at 14,000 rpm.
  iv. Transfer upper phase to a new tube (~150 μl).
  v. Add 113 μl of 5M MH4Oac (Ambion Catalog No. 90706) and mix with a pipette tip.
  vi. Add 660 μl of 100% EtOH (stored at −20° C.) (Sigma Catalog No. E702-3).
  vii. Mix by inverting several times and spin for 30 minutes at 14,000 rpm at 16° C.
  viii. Carefully pour out EtOH (pellet should be visible) and wash the pellet with 500 μl 80% EtOH (stored at −20° C.).
  ix. Spin at 14,000 rpm for 5 minutes at 16° C.
  x. Remove EtOH and air-dry the pellet for about five minutes (pellet can be stored at −20° C.).
  xi. Resuspend the pellet in 8 μl of Gibco water.

Step 2: In vitro Transcription a. Use Ambion Megascript T7 kit (Ambion Catalog No. 1334))
  i. Thaw all reagents except the enzyme mix.
  ii. Mix dNTP mix (per tube):
    1) 2 μl of 75 mM ATP
    2) 2 μl of 75 mM CTP
    3) 2 μl of 75 mM GTP
    4) 2 μl of 75 mM UTP
    5) 2 μl of 10×T7 buffer
    6) 2 μl of 10×T7 enzyme mix
  iii. Add 12 μl of mix to 8 μl of cDNA and mix well.
  iv. Incubate at 37° C. for 6 hours in PCR instrument and then hold at 4° C. if overnight incubation is performed.
b. IVT clean up
  i. Use RNEasy kit for RNA purification (Qiagen Catalog No. 74104) and follow the protocol that is supplied with the product.
c. Determine the concentration of cRNA by OD reading at 260/280 using the following conversion formula: $A_{260} \times$ dilution factor×40=_____ μg/l. The amplification step should give a 3–5 fold increase in the amount of RNA available for labeling (with starting material of 5–10 μg).

Step 3: Labeling Protocol for cRNA or Total Cellular RNA a. Mix 4 μg of cRNA (from the above protocol) with 4 μg of random hexamers (Operon Technologies Catalog No. SP200-10D) and bring the volume up to 14 μl using Gibco water.
b. Incubate at 70° C. for 10 minutes and put on ice. Add, on ice, to cRNA/primer mix:
  i. 6 μl of 5× first strand buffer (Gibco)
  ii. 3 μl of 0.1 M DTT
  iii. 0.6 μl of 50×dNTP mix (50×dNTP mix: 25 mM dCTP, 25 mM dGTP and 10 mM dTTP final concentration; Roche Catalog No. 1969064; all nucleotide stock solutions are 100 mM)

iv. 1.4 µl of Gibco water v. 1 µl of SSII (Gibco)

c. Add 3 ml of 1 mM cy3-dUTP (100 mM final (NEN Catalog No. NEL578) OR 1 mM cy5-dUTP (NEN Catalog No. 577)).

d. Incubate at 42° C. for 30 minutes and then add 1 µl of SSII.

e. Incubate for one additional hour at 42° C.

f. Put samples on ice.

g. RNA Degradation i. Add 1.5 µl of 1M NaOH, 2 mM EDTA solution (should be made fresh each month) per tube and incubate at 65° C. for ten minutes. Put samples on ice.

h. Clean-up of ssDNA i. Add 500 µl of 10 mM Tris pH 7.4 to the labeled probe and apply it to microcon 30 column (Millipore Catalog No. 42410).

ii. Spin at 12,000×g for six minutes (discard the flow-through).

iii. Invert the microcon column into the clean tube and spin for one minute at 1,000×g to collect the sample.

iv. Use a QiaQuick purification kit (Qiagen Catalog No. 28104) and follow the protocol that is supplied with the product.

Step 4: Analysis of Target Quality

Dilute the labeled target 20-fold and measure the OD measurement for cy3 and cy5 as follows. For the cy3 probe, measure $A_{260}$ and $A_{550}$. $A_{260}$ is used to calculate target concentration as described in Step 2. $A_{550}$ is a measure of labeling efficiency. Typical $A_{550}$ should be 0.4 or higher (with the 20-fold dilution). For the cy5 probe, measure $A_{260}$ and $A_{650}$. Typical $A_{650}$ should be 0.03 or higher (with 20-fold dilution).

After ensuring that the target is of sufficient quality, proceed with the hybridization protocol. When starting from 20 µg of total RNA, it is typical to obtain approximately 5 µg of labeled target (equivalent to $A_{260}=0.16$). When starting from 4 µg of cRNA, it is typical to obtain approximately 2 µg of labeled target (equivalent to $A_{260}=0.07$). After labeling of the target one routinely ends up with about 25% of the starting material.

Labeled target prepared as described above may be diluted in CHIPHYBE™ and applied to the arrays as described below.

Step 5: Target Fragmentation

If labeled target is prepared directly from mRNA using poly-dT primers (instead of random hexamers), the length of the cDNAs is significantly larger than when random primers are used. Large length targets have a greater tendency to bind nonspecifically to the glass slide, giving rise to a "granular" background that can interfere with analysis. This problem can be overcome by fragmenting the target cDNA prior to application. Therefore, if large target cDNAs are being employed, fragmentation of the targets is preferred. The steps for target fragmentation are as follows.

a. Mix in a tube: 79 µl of RNase/DNase free water (Gibco Catalog No. 10977); 20 µl of 5× first strand buffer (Gibco Catalog No. 18064-014); and, 1 µl DNase I (Ambion Catalog No. 2222)

b. Add 1 µl of the above mix to 30 µl of probe and incubate at 37° C. for 15 minutes.

c. Denature at 95° C. for five minutes to denature the enzyme and put on ice.

EXAMPLE 9

Protocol for Microarray Hybridization Using the DISCOVERY™

It is recommended that the initial array run on the system follow the protocol outlined below. Based upon results obtained under these conditions, the protocol can then be modified to fine-tune any parameters necessary to optimize conditions for particular array applications. To run the application on the DISCOVERY™ platform, the following steps are taken:

1. Open NEXES® software.
2. Create a protocol by clicking on the "Protocols" button on the main screen. A box appears on the screen with "Create/Edit Protocol" and "Delete Protocol". Click on "Create/Edit Protocol" to open the "NEXES® Protocol Editor" window.
3. Select the "Microarray" procedure under the "Procedure" window.
4. Pre-treatment steps using CHIPPREP™ 1 and 2 in succession are automatically performed on the DISCOVERY™ system, and are not selectable.
5. Set hybridization conditions: click on the box next to "Probe". Two new boxes appear on the screen above "Probe" and four new windows appear. Click on the box next to "Titration" (above the Probe box you have just selected). The "Probe Auto Dispense" will disappear from the screen and two new boxes appear beneath "Titration". Click on the box next to "Manual Application Wet".
6. The "Probe" window is for setting the denaturation and hybridization conditions. Under the "High Temperature" window for "Denaturation" select "70 Deg C." and under the "Denaturation Incubation Time" window select "6 Minutes". It is not recommended to exceed 70° C. denaturation temperature for 6 minutes. Under the "Low Temperature" window for the "Hybridization" select "42 Deg C." (should be maintained between 42° C.–50° C. for DNA targets) and under the "Hybridization Incubation Time" window select "6 hours".
7. Click on the box next to "Stringency Wash #1". A new window "Stringency Wash" and a box next to "High Temp Stringency #1" appears on the screen. Under the "Stringency Wash" window select "1×SSC". Ignore the box next to "High Temperature", under the "Low Temperature" window select "42 degrees" and under the "Incubation Time" window select "10 min".
8. Repeat the above steps for "Stringency Wash #2" and "Stringency Wash #3".
9. Click on the box next to "CHIPCLEAN™".
10. Save the protocol by clicking on the "Save As" button. Windows appear for a protocol name and protocol number. Type in a name for the protocol and select a number in the appropriate boxes. Click on the "Close" button again and the protocol will be saved.
11. Prepare labels and load slides as follows: From the tool bar on the bottom of the main screen, click on the barcode symbol. Click on the "Protocols" button. Highlight the protocol number and name desired in the "Select DISCOVERY™" protocols window. Click on the "Add>>" button once for each protocol barcode label you want to print. Click on the "Close/Print" button. Any additional information that is to appear on the label is entered in the User Prompt boxes. Click the "Print" button. When the last barcode has been printed, click on the "Exit" button. Then be sure all bulk solution containers are properly filled. For a 20 slide run using the microarray procedure, the 2×SSC container must be entirely filled with RIBOWASH™.

12. Place the barcode(s) on the slide(s), loan them carefully on the instrument, close the door and click on the "Run" button. Click on the "Reagents/Reagent Tray Loaded" box and "Reagents Caps Removed" box. Enter the number of slides loaded and click on "Start Run".

13. Following automated pre-treatment of the slides with first the spreading enhancer (CHIPPREP™ 1) and then the blocking solution (CHIPPREP™ 2), labeled target is manually applied to the slides. Typically, 0.5–2 µg of labeled target should be diluted in 200 µl CHIPHYBE™ and applied to the slides. The entire solution should be applied to the slide by touching the slide glass with the pipette tip just below the edge of the barcode label on the slide. The hybridization mixture is then pipetted onto the slide, taking care to avoid bubbles. The automated hybridization protocol is then completed.

14. When the run is completed, the slides are carefully removed from the instrument and the backs of the slides wiped using KIMWIPES™ (Kimberly-Clark, Inc.). The slides are placed bar code down into the slide holder in Reaction Buffer. The slides are washed by dipping into two changes of Reaction Buffer 30 times, followed by 30 dips in water (two separate containers), then dried immediately either by blowing the water off the array surface with a nitrogen gun or by centrifugation at 1000 rpm for 5 minutes. Following drying, the slides should be stored in a light-tight container until scanned.

EXAMPLE 10

Comparison of Automated Hybridization to a Manual Method

Figure 2:
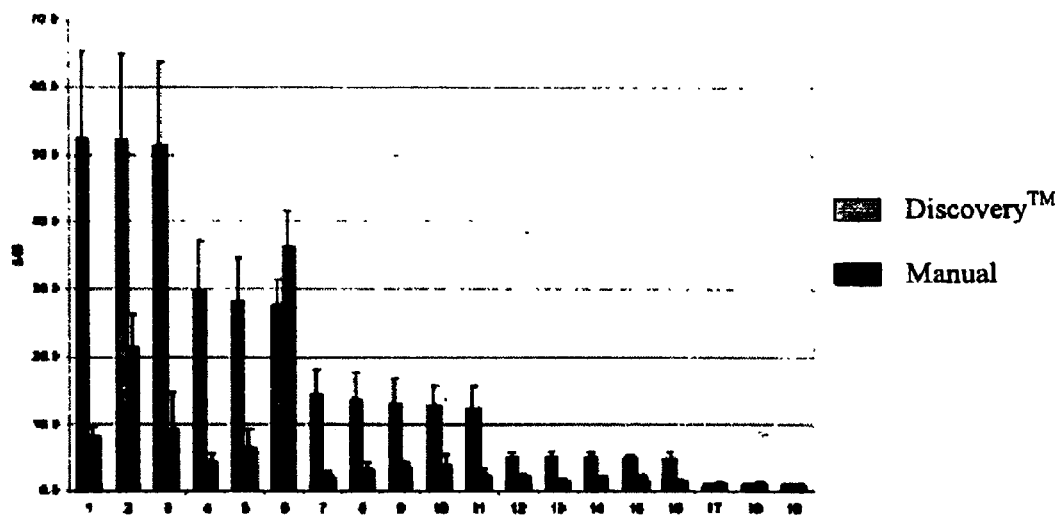
FIG. 2 displays the results of a comparative study demonstrating the superior sensitivity of automated hybridization on the DISCOVERY™ system relative to the manual method (signal-to-background).

The results of an exemplary experiment are shown in FIG. 2. The figure shows the results of a comparative study demonstrating the superior sensitivity of automated hybridization on the DISCOVERY™ instrument as compared to manual techniques. The data was generated from 19 different genes on eight microarrays: four run manually and four run using the automated method. As shown in FIG. 2, automated hybridization according to the invention produced a significantly higher signal to background ratio than the manual protocol for the vast majority of the 19 genes tested.

The coefficient of variation across four microarrays, comparing automated hybridization on the DISCOVERY™ instrument versus two manual hybridizations, is shown below in Table 1:

TABLE 1

Coefficient of Variation (CV): Automated vs. Manual Hybridization

|  | % CV |
| --- | --- |
| DISCOVERY ™ | 15.1 |
| Manual 1 | 16.7 |
| Manual 2 | 19.4 |

Although certain presently preferred embodiments of the invention have been described herein, it will be apparent to those of skill in the art to which the invention pertains that variations and modifications of the described embodiment may be made without departing from the spirit and scope of the invention. Accordingly, it is intended that the invention be limited only to the extent required by the following claims and the applicable rules of law. All of the articles, books, patents, patent applications, and other references cited in this patent application are hereby incorporated by reference.

The invention claimed is:

1. An aqueous composition, comprising sodium chloride; sodium phosphate dibasic; sodium phosphate monobasic; EDTA; first primary prehybridization detergent; second primary prehybridization detergent; and formalin.

2. The composition of claim 1, comprising 0.15–1.5 M sodium chloride; 8–80 mM sodium phosphate dibasic; 2–20 mM sodium phosphate monobasic; 1–10 mM EDTA; 0.0125–0.125% first primary prehybridization detergent; 0.00375–0.0375% second primary prehybridization detergent; and 10–40% formalin.

3. The composition of claim 2, comprising 0.3 M sodium chloride; 16 mM sodium phosphate dibasic; 4 mM sodium phosphate monobasic; 2 mM EDTA; 0.025% first primary prehybridization detergent; 0.0075% second primary prehybridization detergent; and 30% formalin.

4. An aqueous composition consisting essentially of 0.4–8.2 mM sodium citrate; 1.8–10 mM citric acid; 0.1–1% cell conditioning preservative; and 0.05–5% cell conditioning detergent.

5. The composition of claim 4, comprising 8.2 mM sodium citrate; 1.8 mM citric acid; 0.05% cell conditioning preservative; and 0.1% cell conditioning detergent.

6. An aqueous composition, comprising sodium chloride; phosphate buffer; EDTA; and one or more nonionic detergents wherein the nonionic detergents are first wash detergent and second wash detergent.

7. The composition of claim 6, comprising 0.1–0.5 M sodium chloride; 5–30 mM sodium phosphate dibasic; 1–10 mM sodium phosphate monobasic; 0.5–5 mM EDTA; 0.01–0.1% first wash detergent; and 0.0025–0.025% second wash detergent.

8. The composition of claim 7, comprising 0.3 M sodium chloride; 16 mM sodium phosphate dibasic; 4 mM sodium phosphate monobasic; 2 mM EDTA; 0.025% first wash detergent; and 0.0075% second wash detergent.

9. The composition of claim 6, comprising 0.5–2.5 M sodium chloride; 25–150 mM sodium phosphate dibasic; 5–50 mM sodium phosphate monobasic; 2.5–25 mM EDTA; 0.05–0.5% first wash detergent; and 0.0125–0.125% second wash detergent.

10. The composition of claim 9, comprising 1.5 M sodium chloride; 80 mM sodium phosphate dibasic; 20 mM sodium phosphate monobasic; 10 mM EDTA; 0.125% first wash detergent; and 0.0375% second wash detergent.

11. An aqueous composition, comprising 4×–8×SSPE and 8–12% spreading enhancer detergent.

12. The composition of claim 11, comprising 6×SSPE and 10% spreading enhancer detergent.

13. A reagent kit for use in automated in situ hybridization, comprising:
(a) an aqueous composition, comprising 0.15–1.5 M sodium chloride; 8–80 mM sodium phosphate dibasic; 2–20 mM sodium phosphate monobasic; 1–10 mM EDTA; 0.0125–0.125% first primary prehybridization detergent; 0.00375–0.0375% second primary prehybridization detergent; and 10–40% formalin;
(b) an aqueous composition, comprising 0.1–1 N HCl; and
(c) an aqueous composition, comprising 1×–5×SSPE; 10–50% dextran sulfate sodium salt, average molecular weight 10,000; 50–80% formamide; and 0.01–1% in situ hybridization detergent.

14. The reagent kit of claim 13, comprising:
(a) an aqueous composition, comprising 0.3 M sodium chloride; 16 mM sodium phosphate dibasic; 4 mM sodium phosphate monobasic; 2 mM EDTA; 0.025% first primary prehybridization detergent; 0.0075% second primary prehybridization detergent; and 30% formalin;
(b) an aqueous composition, comprising 0.3 N HCl; and
(c) an aqueous composition, comprising 2×SSPE; 20% dextran sulfate sodium salt, average molecular weight 10,000; 80% formamide; and 0.05% in situ hybridization detergent.

15. A reagent kit for use in automated microarray hybridization, comprising:
(a) an aqueous composition, comprising 4×–8×SSPE and 8–12% spreading enhancer detergent;
(b) an aqueous composition, comprising phosphate buffer of 10–200 mM total salt concentration; 5–15% hydrolyzed casein; and 0.005–1% nonionic detergent;
(c) an aqueous composition, comprising 2–6×SSPE; 17.5–22.5% dextran sulfate sodium salt, average molecule weight 10,000; and 10–50% formamide; and
(d) an aqueous composition, comprising 0.1–5% microarray cleaning detergent.

16. The reagent kit of claim 15, comprising:
(a) an aqueous composition, comprising 6×SSPE and 10% spreading enhancer detergent;
(b) an aqueous composition, comprising 75 mM potassium phosphate; 25 mM sodium phosphate; 55 mM NaCl; 13.4% hydrolyzed casein; and 0.05% blocking detergent;
(c) an aqueous composition, comprising 6×SSPE; 20% dextran sulfate sodium salt, average molecule weight 10,000; and 10% formamide; and
(d) an aqueous composition, comprising 1% microarray cleaning detergent.

17. A method for automated in situ hybridization, comprising:
(a) exposing a cell or tissue sample to a prehybridization solution including at least one prehybridization detergent;
(b) exposing the sample to a cell conditioning reagent;
(c) exposing the sample to a nucleic acid probe in a hybridization solution;
(d) exposing the sample to a wash solution;
(e) exposing the sample to a post-hybridization fixing solution; and
(f) analyzing the sample for hybridization between the probe and a target nucleic acid;
wherein steps (a)–(e) are performed using an automated instrument.

18. The method of claim 17, wherein the prehybridization solution comprises 0.3 M sodium chloride; 16 mM sodium phosphate dibasic; 4 mM sodium phosphate monobasic; 2 mM EDTA; 0.025% first primary prehybridization detergent; 0.0075% second primary prehybridization detergent; and 30% formalin.

19. The method of claim 17, wherein the prehybridization solution comprises 0.3 N HCl.

20. The method of claim 17, wherein the cell conditioning reagent comprises 8.2 mM sodium citrate; 1.8 mM citric acid; 0.05% cell conditioning preservative; and 0.1% cell conditioning detergent.

21. The method of claim 17, wherein the hybridization solution comprises 2×SSPE; 20% dextran sulfate sodium salt, average molecular weight 10,000; 80% formamide; and 0.05% in situ hybridization detergent.

22. The method of claim 17, wherein the hybridization solution comprises 6×SSPE; 20% dextran sulfate sodium salt, average molecular weight 10,000; and 10% formamide.

23. The method of claim 17, wherein the wash solution comprises 0.3 M sodium chloride; 16 mM sodium phosphate dibasic; 4 mM sodium phosphate monobasic; 2 mM EDTA; 0.025% first wash detergent; and 0.0075% second wash detergent.

24. The method of claim 17, comprising:
(a) exposing a cell or tissue sample to a composition comprising 0.3 M sodium chloride; 16 mM sodium phosphate dibasic; 4 mM sodium phosphate monobasic; 2 mM EDTA; 0.025% first primary prehybridization detergent; 0.0075% second primary prehybridization detergent; and 30% formalin;
(b) exposing the sample to a composition comprising 0.3 N HCl;
(c) exposing the sample to a composition comprising 8.2 mM sodium citrate; 1.8 mM citric acid; 0.05% cell conditioning preservative; and 0.1% cell conditioning detergent;
(d) exposing the sample to a nucleic acid probe in a composition comprising 2×SSPE; 20% dextran sulfate sodium salt, average molecular weight 10,000; 80% formamide; and 0.05% in situ hybridization detergent;

(e) exposing the sample to a composition comprising 0.3 M sodium chloride; 16 mM sodium phosphate dibasic; 4 mM sodium phosphate monobasic; 2 mM EDTA; 0.025% first wash detergent; and 0.0075% second wash detergent;

(f) exposing the sample to a composition comprising 0.3 M sodium chloride; 16 mM sodium phosphate dibasic; 4 mM sodium phosphate monobasic; 2 mM EDTA; 0.025% first primary prehybridization detergent; 0.0075% second primary prehybridization detergent; and 30% formalin; and (g) analyzing the sample for hybridization between the probe and a target nucleic acid;

wherein steps (a)–(f) are performed using an automated instrument.

25. A method for automated microarray hybridization, comprising:

(a) exposing a microarray to a spreading enhancer solution that includes at least one nonionic detergent;

(b) exposing the microarray to a blocking solution;

(c) exposing the microarray to a target nucleic acid in a hybridization solution;

(d) exposing the microarray to a wash solution;

(e) exposing the microarray to a microarray cleaning solution; and (f) analyzing the microarray for hybridization between a nucleic acid probe and the nucleic acid target;

wherein steps (a), (b), (d), and (e) are performed using an automated instrument.

26. The method of claim 25, wherein the spreading enhancer solution comprises 6×SSPE and 10% spreading enhancer detergent.

27. The method of claim 25, wherein the blocking solution comprises 75 mM potassium phosphate; 25 mM sodium phosphate; 55 mM NaCl; 13.4% hydrolyzed casein; and 0.05% blocking detergent.

28. The method of claim 25, wherein the hybridization solution comprises 6×SSPE; 20% dextran sulfate sodium salt, average molecule weight 10,000; and 10% formamide.

29. The method of claim 25, wherein the wash solution comprises 0.3 M sodium chloride; 16 mM sodium phosphate dibasic; 4 mM sodium phosphate monobasic; 2 mM EDTA; 0.025% first wash detergent; and 0.0075% second wash detergent.

30. The method of claim 25, wherein the microarray cleaning solution comprises 0.1–5% microarray cleaning detergent.

31. The method of claim 25, wherein the microarray cleaning solution comprises 1% microarray cleaning detergent.

32. The method of claim 25, comprising:

(a) exposing a microarray to a composition comprising 6×SSPE and 10% spreading enhancer detergent;

(b) exposing the microarray to a composition comprising 75 mM potassium phosphate; 25 mM sodium phosphate; 55 mM NaCl; 13.4% hydrolyzed casein; and 0.05% blocking detergent;

(c) exposing the microarray to a composition comprising 6×SSPE; 20% dextran sulfate sodium salt, average molecule weight 10,000; and 10% formamide;

(d) exposing the microarray to a composition comprising 0.3 M sodium chloride; 16 mM sodium phosphate dibasic; 4 mM sodium phosphate monobasic; 2 mM EDTA; 0.025% first wash detergent; and 0.0075% second wash detergent;

(e) exposing the microarray to a composition comprising 1% microarray cleaning detergent; and (f) analyzing the microarray for hybridization between a nucleic acid probe and the nucleic acid target;

wherein steps (a), (b), (d), and (e) are performed using an automated instrument.

33. The reagent kit of claim 15 comprising:

(a) an aqueous composition, comprising 1.5M NaCl and 10% spreading enhancer detergent;

(b) an aqueous composition, comprising 75 mM potassium phosphate; 25 mM sodium phosphate; 55 mM NaCl; 13.4% hydrolyzed casein; and 0.05% blocking detergent;

(c) an aqueous composition, comprising 6×SSPE; 20% dextran sulfate sodium salt, average molecule weight 10,000; and 60% formamide; and (d) an aqueous composition, comprising 1% microarray cleaning detergent.

* * * * *

SEQUENCE LISTING

```
<160> NUMBER OF SEQ ID NOS: 1

<210> SEQ ID NO 1
<211> LENGTH: 63
<212> TYPE: DNA
<213> ORGANISM: Artificial Sequence
<220> FEATURE:
<223> OTHER INFORMATION: cDNA primer used in Example 8.

<400> SEQUENCE: 1
ggccagtgaa ttgtaatacg actcactata gggaggcggt tttttttttt tttttttttt      60
ttt                                                                    63
```